United States Patent [19]
Seeman et al.

[11] Patent Number: 5,278,051
[45] Date of Patent: Jan. 11, 1994

[54] CONSTRUCTION OF GEOMETRICAL OBJECTS FROM POLYNUCLEOTIDES

[75] Inventors: Nadrian C. Seeman, New York; Yuwen Zhang, Queens, both of N.Y.

[73] Assignee: New York University, New York, N.Y.

[21] Appl. No.: 805,564

[22] Filed: Dec. 12, 1991

[51] Int. Cl.$^5$ .............................................. C12N 15/10
[52] U.S. Cl. ................................ 435/91.52; 536/23.1; 536/24.2; 435/91.3; 435/91.51
[58] Field of Search ...................... 435/91; 935/16, 88, 935/10; 536/27

[56] References Cited

PUBLICATIONS

Chen et al., "A Specific Quadrilateral Synthesized from DNA Branced Juntions", *J. Am. Chem. Soc.*, 111: 6402-6407 (1989).
Seeman, Nadrian C., "Nanoscale Assembly and Manipulation of Branched DNA: A Biological Starting Point for Nanotechnology", *Nanocon Proceedings*, pp. 101-107, 1989.
Petrillo et al., "The Ligation and Flexibility of Four--Arm DNA Junctions", *Biopolymers*, 27: 1337-1352, 1988.
Robinson et al., "The design of a biochip: a self-assembling molecular-scale memory device", *Protein Engineering*, 1(4): 295-300, 1987.
Ma et al., "Three-arm nucleic acid junctions are flexible", *Nucleic Acids Research*, 14(24): 9745-9753, 1986.
Kallenbach et al., "An immobile nucleic acid junction constructed from oligonucleotides", *Nature*, 305(5937): 829-831, 1983.
Seeman, Nadrian C. "Nucleic Acid Junctions and Lattices", *J. Theor. Biol.*, 99: 237-247, 1982.
Chen et al., "Construction and Analysis of Monomobile DNA Junctions", *Biochemistry*, 27: 6032-6038, 1988.
Beattie et al., "Solid-phase gene assembly", *Nature*, 352: 548-549, 1991.
Seeman, Nadrian C., "Interactive design and manipulation of macro-molecular architecture utilizing nucleic acid junctions", *Journal of Molecular Graphics*, 3(2): 34-39, 1985.
Seeman, Nadrian C., "Design of Immobile Nucleic Acid Junctions", *Biophys. J.*, 44:201-209, 1983.
Seeman, Nadrian C., "Nucleic Acid Junctions: The Tensors of Life?", *Nucleic Acids: The Vectors of Life*, 183-200, 1983.
Seeman et al., "Gel electrophoretic analysis of DNA branched junctions", *Electrophoresis*, 10: 345-354, 1989.
Piccirilli et al., "Enzymatic incorporation of a new base pair into DNA and RNA extends the genetic alphabet", *Nature*, 343, 33-37, 1990.
Murchie et al., "Fluorescence energy transfer shows that the four-way DNA junction is a right-handed cross of antiparallel molecules", *Nature*, 341: 763-766, 1989.
Cooper et al., "Geometry of a branched DNA structure in solution", *Proc. Natl. Acad. Sci.*, 86: 7336-7340, 1989.

*Primary Examiner*—Richard A. Schwartz
*Assistant Examiner*—David Guzo
*Attorney, Agent, or Firm*—Browdy and Neimark

[57] ABSTRACT

One, two and three dimensional structures may be synthesized or modified from polynucleotides. A core structure is expanded by cleavage of a loop with a restriction endonuclease and ligating another polynucleotide to the sticky ends so that the recognition site of the restriction enzyme is not reformed. This process is repeated as many times as necessary to synthesize any desired structure. The structures formed have a wide range of uses.

13 Claims, 10 Drawing Sheets

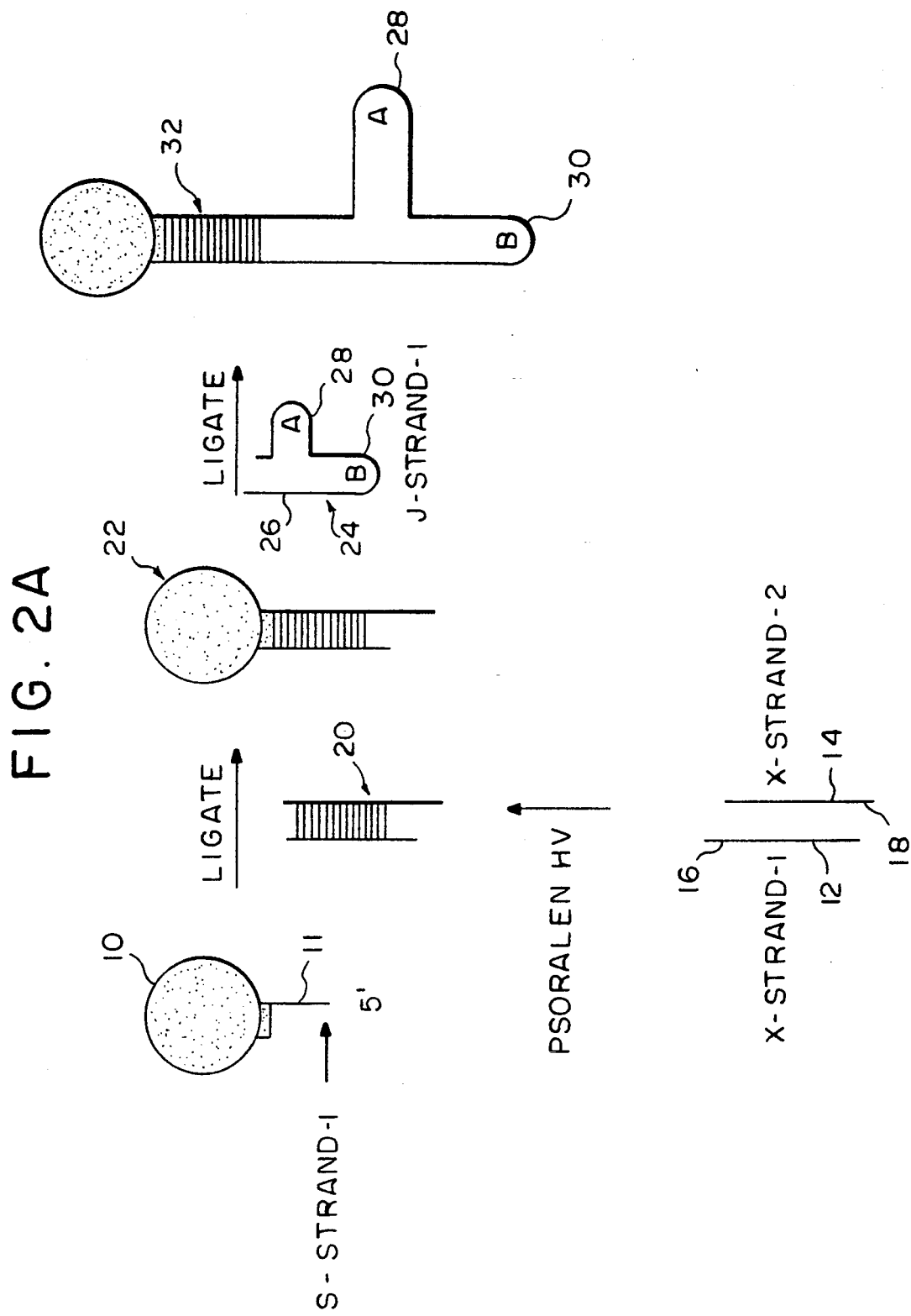

FIG. 2B

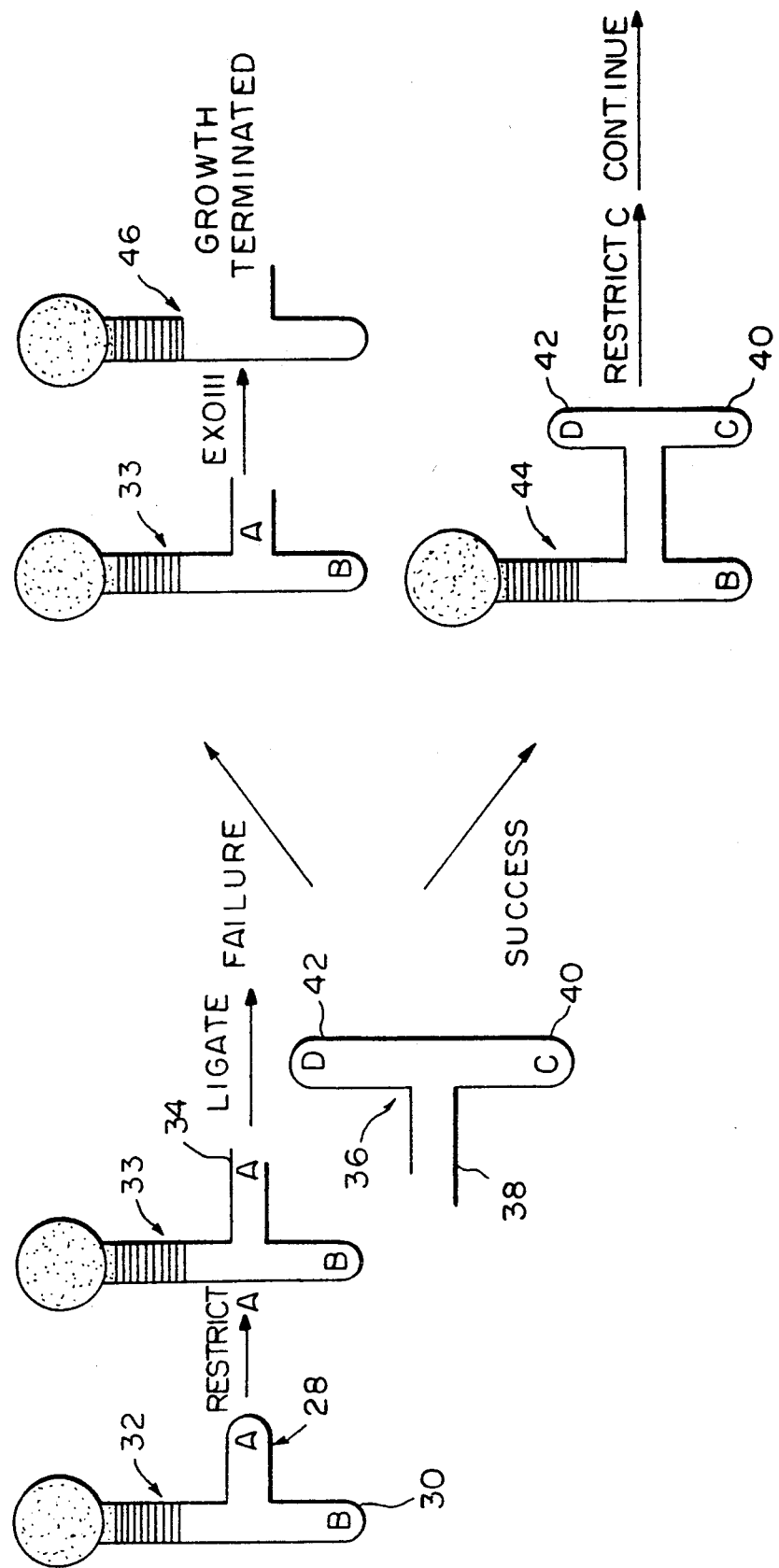

FIG. 6
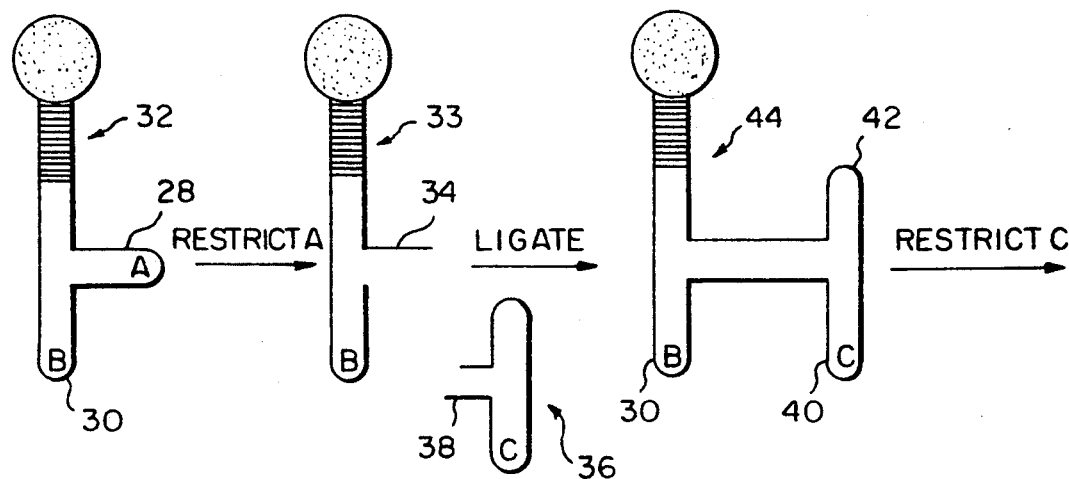
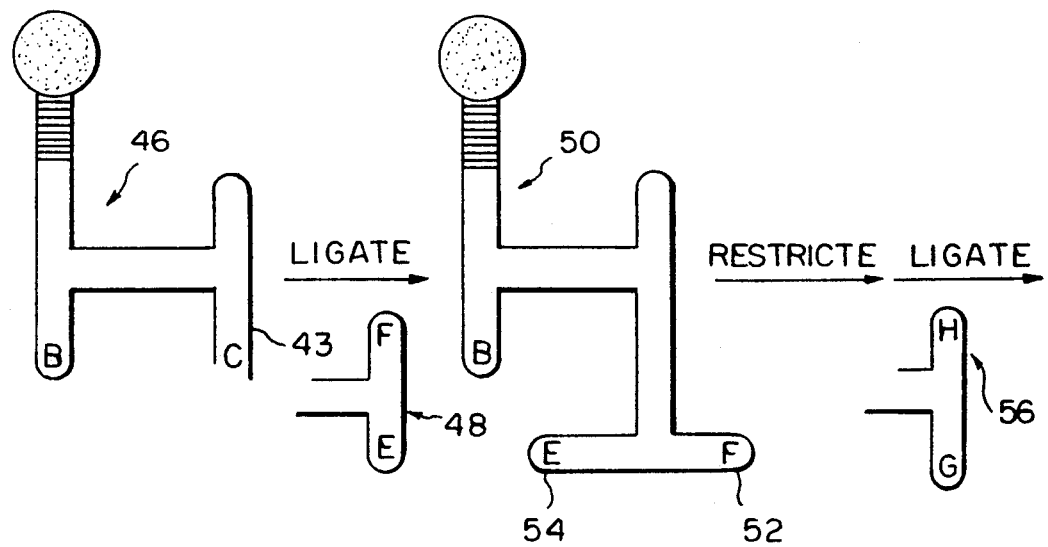
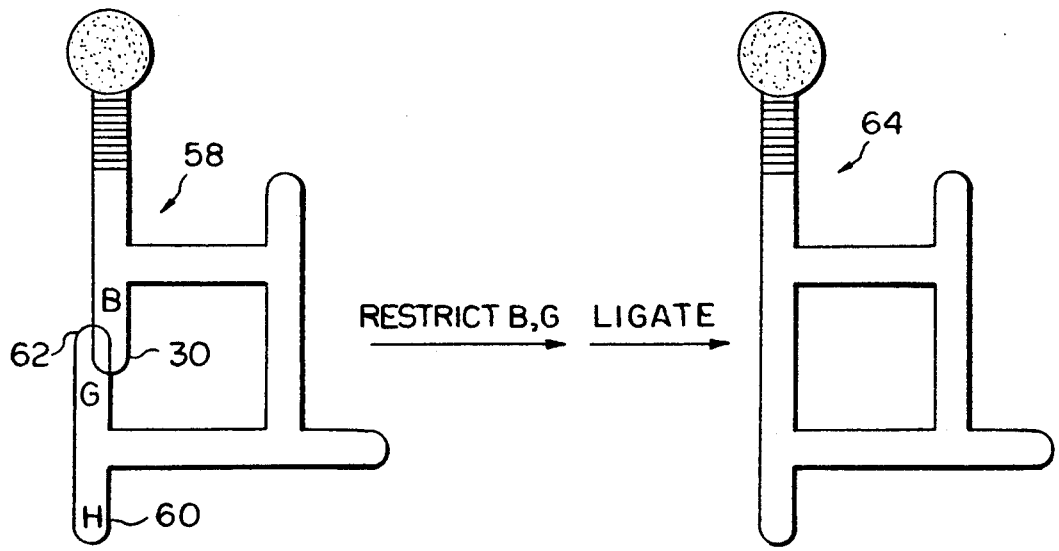

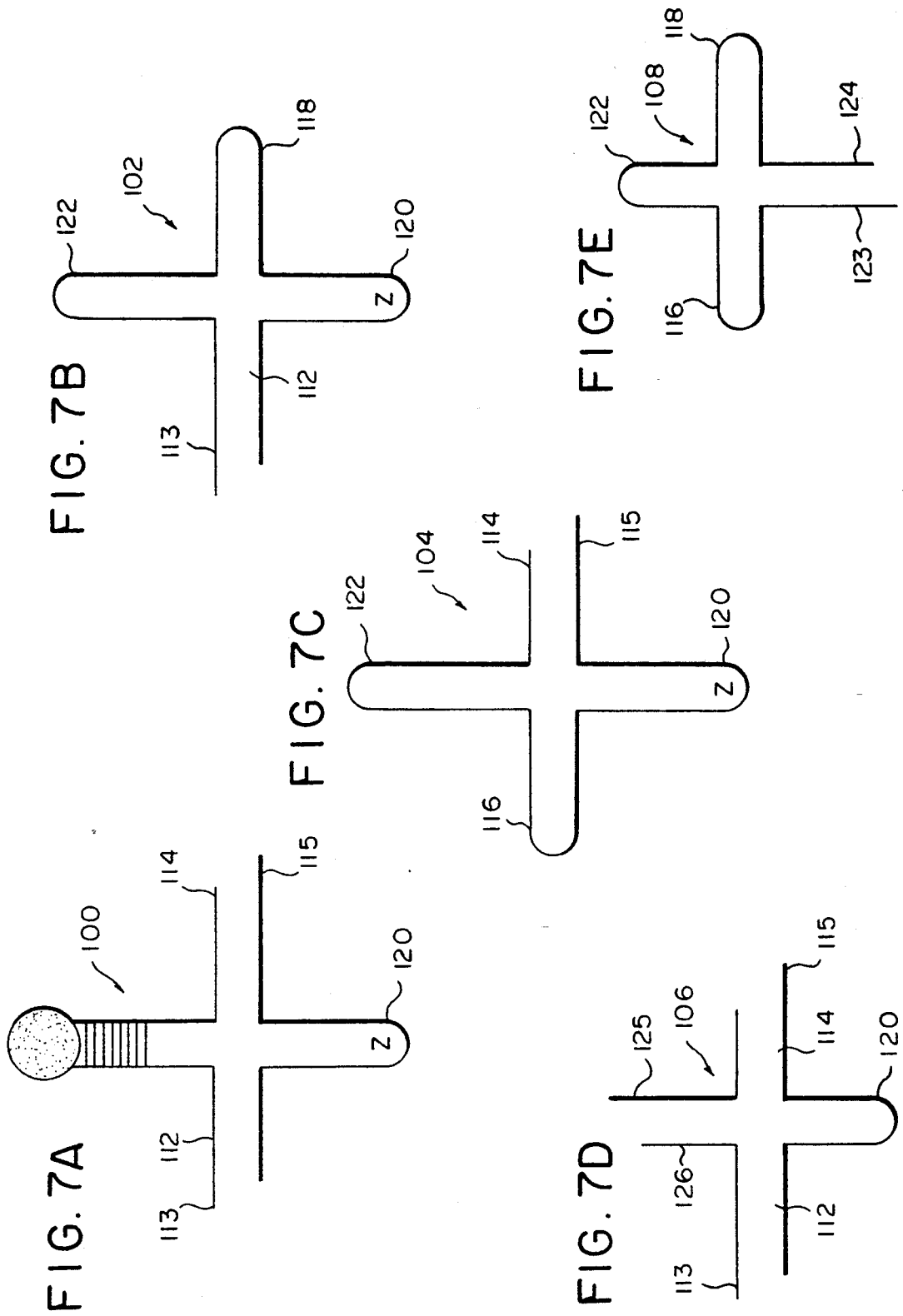

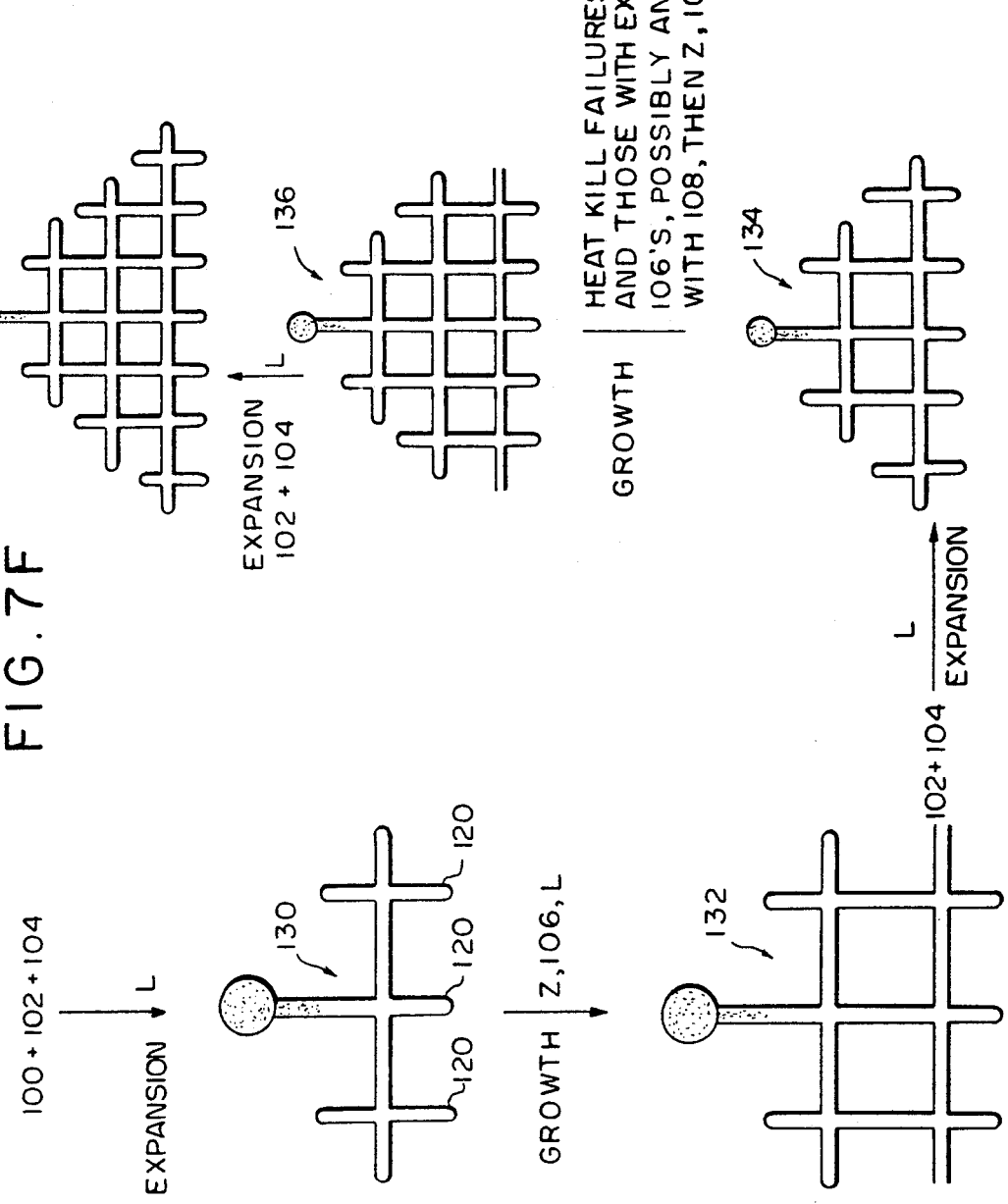

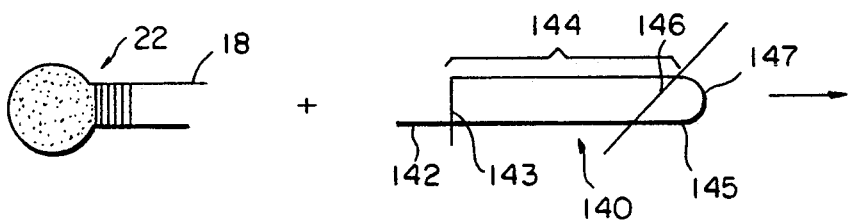
FIG. 8A
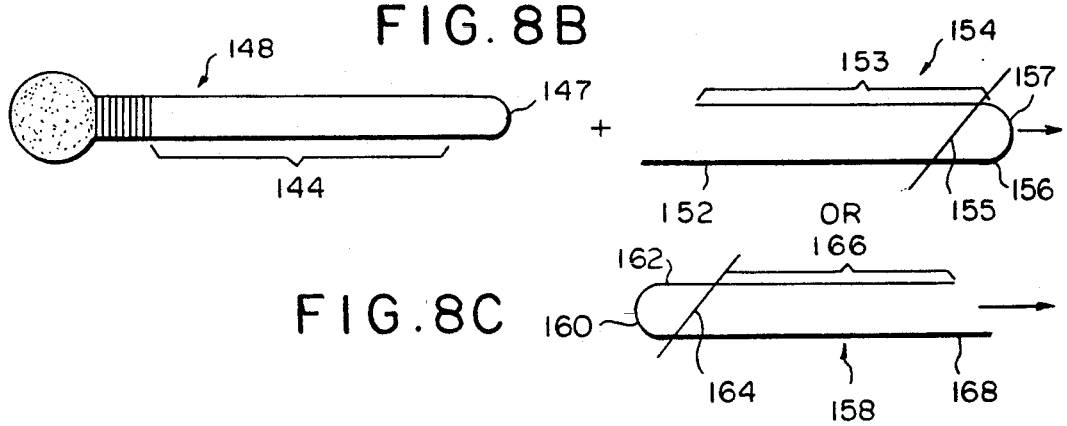
FIG. 8B
FIG. 8C
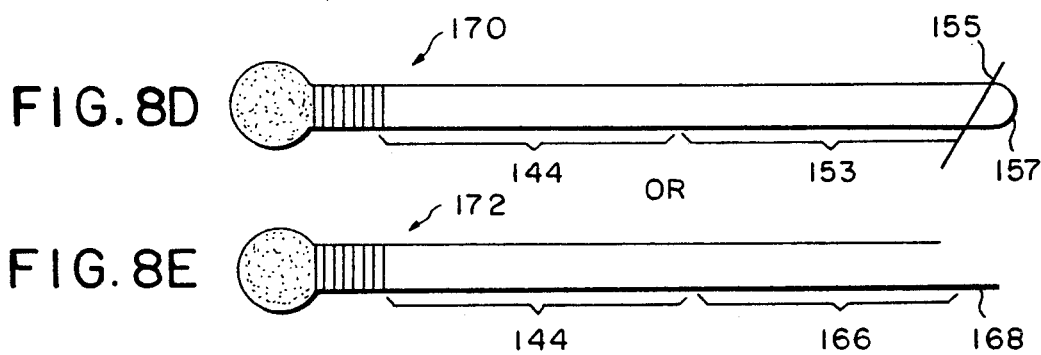
FIG. 8D
FIG. 8E

CONSTRUCTION OF GEOMETRICAL OBJECTS FROM POLYNUCLEOTIDES

This experiments performed in this applications were supported in part by the Office of Naval Research, grant number N00014-89-J-3078 and the National Institutes of Health, grant number GM-29554 The United States Government has certain rights to this patent application.

CROSS REFERENCE TO RELATED APPLICATION

The present application is related to copending application Ser. No. 07/639,684, filed Jan. 10, 1991, the entire contents of which are hereby incorporated by reference.

FIELD OF THE INVENTION

The present invention relates to methods and reagents for preparing predetermined two dimensional and three dimensional structures of polynucleotides.

BACKGROUND TO THE INVENTION

There is considerable interest in the development of macromolecular chemical systems with well-defined structural properties for use as molecular scaffolding to orient and juxtapose other molecules. The motivations for pursuing these constructions include the formation of macromolecular 'zeolite' lattices to enable diffraction analysis of complex guest molecules that are not readily crystallized (Seeman, N. C., In: *Biomolecular Stereodynamics*, ed. by R. H. Sarma, Academic Press, New York, (1981) pp. 269–277; Seeman, N. C., *J. Theor., Biol.*, 99: 237–247 (1982); Seeman, N. C., J. Biomol., Str. & Dyns., 3: 11–34 (1985)); the caging of active biological macromolecules to form new multi- functional enzymes ( Chen, et al., *J. Am. Chem Soc.*, 111: 6402–6407 (1989)); drug delivery systems for therapeutic macromolecules (Seeman, *DNA and Cell Biology*, 10: 475–486 (1991)); mechanical control on the nanometer scale (Seeman, In *NANOCON Proceedings*, ed. by J. Lewis et al., Nanocon, Bellevue Wash., pp. 101–123 (1989)), and the assembly of molecular electronic components (Robinson, et al., *Prot. Eng.*, 1: 295–300 (1987); Hopfield, et al., *Science.* 241: 817–820 (1988)).

One of the major goals of both biotechnology and nanotechnology is the assembly of novel biomaterials that can be used for analytical, industrial or therapeutic purposes (Feynman, R. P., In *Miniaturization*, ed. by H. D. Gilbert, Reinhold Publishing Corp., New York, 282–296 (1961); Drexler, K. E., *Proc. Nat. Acad. Sci.* (USA), 7: 5275–5278 (1981)). A particular aim is to construct individual objects and devices on the nanometer scale, utilizing the informational macromolecules, e.g., polypeptides and polynucleotides, of biological systems.

Nature provides many examples of elegant polypeptide or polynucleotide constructs on a nanometer scale. For example, the type of subcellular organelle known as a ribosome is a sophisticated machine constructed of polynucleotides and polypeptides. As is well known to the art, a ribosome functions in a machine-like manner in order to "read" the genetic sequence coded by a messenger ribonucleic acid (mRNA) strand and to generate the corresponding polypeptide.

Polypeptides play a variety of prominent functional roles in living cells, including enzymatic, regulatory and structural activities; hence, substantial effort has gone into the engineering of polypeptides (Leatherbarow, et al., *Protein Eng.*, 1: 7–16 (1986); DeGrado, et al., *Science*, 243: 622–628 (1989); Anthony-Cahill, et al., *Trends in Biochem. Sci.*, 14: 400–403 (1989)). However, less attention has been paid to the structural possibilities of nucleic acids The most stable form of naturally-occurring DNA is a linear double helical molecule (Watson, et al., *Nature*, 171: 737–738 (1953)), with limited potential for the construction of complex objects.

During the past several years, a number of investigations of the physical properties of deoxyribonucleic acid (DNA) branched junctions have been published (Kallenbach, et al. , *Nature*, 305; 829–831 (1983); Kallenbach, et al., *J. Biomol. Str. and Dyns.*, 1: 158–168 (1983); Seeman, et al., *Prog. Clin. & Biol. Res.*, 172A: 99–108 (1985); Wemmer, et al., *Biochemistry*, 24: 5745–5749 (1985); Marky, et al., *Biopolymers*, 26: 1621–1634 (1987); Churchill, et al., *Proc. Nat. Acad. Sci.* (USA), 85: 4653–4656 (1988); Chen, et al., *Biochemistry*, 27: 6032–6038 (1988); Cooper, et al., *J. Mol Biol.*, 198: 711–719 (1987); Duckett, et al., *Cell*, 55: 79–89 (1988); Seeman, N. C., *Electrophor.*, 10: 345–354 (1989); Cooper, et al., *Proc. Nat. Acad. Sci.*, (USA) 86: 7336–7340 (1989); Murchie, et al., *Nature*, 341: 763–766 (1989)). Their susceptibility to resolving enzymes have also been reported (Duckett, et al., *Cell*, 55: 79–89 (1988); Evans, et al., *J. Biol. Chem.*, 262: 14826–14836 (1987); Dickie, et al., *J. Biol. Chem.*, 262: 14826–14836 (1987); Mueller, et al., *Proc. Nat. Acad. Sci.* (USA), 85: 9441–9445 (1988)). These studies have been stimulated by the role of branched DNA molecules as intermediates in the process of genetic recombination (Holliday, R., *Genet. Res.*, 5: 282–304 (1964)).

In addition, the possibility of using branched DNA molecules to construct nanometer scale (also referred to herein as "nanoscale") objects has been explored In prior work a series of macrocycles (cyclic trimers, tetramers, etc.) was formed by oligomerizing 3-arm junctions (Ma, et al., *Nucl. Acids.Res.*, 14: 9745–9753 (1986)) or 4-arm junctions (Petrillo, et al., *Biopolymers*, 27: 1337–1352 (1988) containing a pair of complementary cohesive ends. The presence of numerous closed products from those ligations indicates a large degree of flexibility in the angles between arms (over long ligation times), regardless of how well-defined the structure of an individual junction may appear to be (Seeman, et al., *Electrophor.*, 10: 345–354 (1989); Cooper, et al., *Proc. Nat. Acad. Sci.* (USA), 86: 7336–7340 (1989); Murchie, et al., *Nature.* 341: 763–766 (1989)).

Each of these studies has produced a closed object that may be described as 2-connected (Wells, A. F., *Three-dimensional Nets and Polyhedra*, John Wiley & Sons, New York, p. 3 (1977)). Although sharp kinks are introduced into the constructs by the presence of the junctions, the closed figures formed are essentially cyclic flexed variations on a linear theme.

The laboratory of the present inventors have made three dimensional DNA constructs where the DNA chains together formed a cube (Chen et al, *Nature*, 350: 631–633 (1991)), and copending patent application Ser. No. 07/639,684 filed Jan. 10, 1991, the entire contents of which are hereby incorporated by reference). This structure was formed from a series of preformed DNA constructs designed to specifically hybridize to each other.

Control over which arms are reactive in this previously described synthesis derives only from the presence or absence of 5' phosphates on particular exocyclic arms. Thus, only two logical stages of synthesis are possible if all strands are present throughout the synthesis: (i) initial phosphorylation of certain strands followed by ligation, and (ii) phosphorylation of the remaining strands in the intact molecule followed by a second ligation. Undesirable intermediate steps (denaturation and reconstitution) are necessary in the previous protocol, because it is not possible to purify side-products and failure products of the first reaction from the target product under native conditions.

Although it is possible to treat the ends of each branched component as individually accessible, the formation of closed geometrical objects entails two fundamentally different types of reactions, intermolecular additions and intramolecular cyclizations. Additions are favored usually by high concentrations of reactants, but cyclizations are favored by low concentrations. Thus, unless one wishes to run all the additions in a single step and all the cyclizations in a second one (sometimes possible, but unwise), greater control over multi-step synthesis must be obtained.

The synthesis of more complex structures from DNA will require greater control than that available in the synthesis of the cube-like object. Accordingly, the present inventors have developed a new methodology for the synthesis of DNA geometrical objects, in which each ligation may be separately performed.

Thus, it can be readily appreciated that the easily manipulated changes to form or modify a three dimensional structure of double stranded polynucleotides would be useful and a highly desirable advance over the current state of technology.

SUMMARY OF THE INVENTION

By means of the present invention, DNA, RNA and similar polymers may be produced by synthesizing a double stranded segment, preferably with a loop at one end, cleaving the end of the double stranded portion having the loop, and ligating to the cleaved end a new double stranded segment, previously synthesized to have an end which will ligate to the cleaved end of the first segment and to have another loop at another end having a sequence recognizable by a predetermined restriction endonuclease, the ligation causing an increase in the size of the structure. The cleavage of the first loop is accomplished in a controlled manner by creating a unique site for a restriction enzyme which does not have its enzyme recognition site reformed after ligation of the new segment of polynucleotide. This process may be repeated as many times as desired to produce almost any structure one can imagine. It is particularly useful for preparation of two and three dimensional structures.

Furthermore, by leaving one or more restriction sites in the structure, it may be modified at a later time after manufacturing. Thus, modifications may be made to fine tune the structure once it is in use or to fix it in a particular position.

The structure being formed may have multiple numbers of a particular restriction site. This permits mass additions to the preexisting structure and lends itself very well to automation and mass production using the techniques known in the fields of solid phase nucleic acid synthesis and solid phase peptide synthesis.

The ability to construct functional artificial components on a nanometer scale from polynucleotides will provide the capability of creating artificial tools and reagents able to mimic the function of natural subcellular organelles and to perform other useful functions, not necessarily present in the natural state, for diagnostic, therapeutic or industrial purposes. For example, such a construct would provide a useful three-dimensional scaffolding upon which enzymatic or antibody binding domains may be linked to provide high density multivalent processing sites to link to and solubilize otherwise insoluble enzymes, or to entrap, protect and deliver a variety of molecular species, and the like. Alternatively, the construct may form a molecular device alone which has a variety of uses such as in the field of electronic devices.

BRIEF DESCRIPTION OF THE DRAWINGS

FIG. 2A is a reaction scheme showing preparation of a solid support. A solid support is represented as the gray ball, and a crosslink is illustrated as crossbars. The strand being added represents a polynucleotide with two hairpin loops.

FIG. 2B is an enlargement of J-Strand-1, SEQ ID NO:10 showing its two-dimensional structure.

FIG. 3 is a diagram showing a protocol for solid-state synthesis with exonuclease III destruction of unligated material.

FIG. 6 is a diagram showing the synthesis of a quadrilateral.

FIG. 7 (parts A-F) is a diagram showing the synthesis of a large lattice.

FIG. 8 (parts A-E) is a diagram showing the assembly of portions of genes.

DETAILED DESCRIPTION OF PREFERRED EMBODIMENTS

Figure 1A:
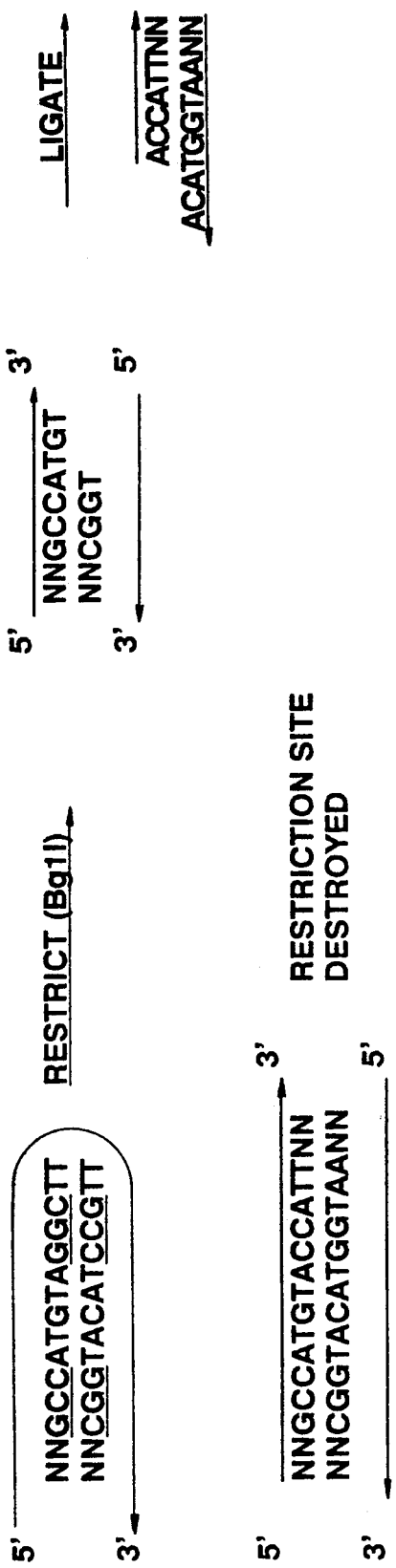
FIG. 1 (parts A and B) shows reaction scheme protocols for elimination of restriction sites using enzymes that recognize an interrupted sequence (FIG. 1A) or that recognize a sequence which is distant from their scission site (FIG. 1B).

The procedure of the present invention uses the cleavage of individual double stranded DNA loops or double stranded segments to form free cohesive ends. This is analogous to deprotection of a functional group for use in a reaction. It is logically similar to detritylation in solid-phase oligonucleotide synthesis (Caruthers, M. H., In: Chemical and Enzymatic Synthesis of Gene Fragments, eds. Gassen, H. G. and Lang, A., (Verlag Chemie, Weinheim) 1982, pp. 71-79). The step-wise deprotection gives control over the formation of individual edges. The deprotection restriction endonucleases are examples of what will hereafter be called "growth enzymes".

There are a number of restriction enzymes that (1) recognize interrupted sequences, (2) recognize asymmetric sequences, (3) recognize sequences that are removed from the site of scission, (4) cut bluntly, or (5) in combination with a second different restriction enzyme, cut at two different sites which, once cut, form sticky ends complementary to each other but upon ligation to each other, do not reform either restriction site. Useful examples of the first group, which recognize interrupted sequences, include:

| ENZYME | GROUP I RECOGNITION SEQUENCE AND CLEAVAGE SITE |
|---|---|
| AlwNI | CAGNNN ↓ CTG SEQ ID NO: 1 |
| BglI | GCCNNNN ↓ NGGC SEQ ID NO: 2 |
| BstXI | CCANNNNN ↓ NTGG SEQ ID NO: 3 |
| DraIII | CACNNN ↓ GTG SEQ ID NO: 4 |
| PflMI | CANNNN ↓ NTGG SEQ ID NO: 5 |
| SfiNI | GGCCNNNN ↓ NGGCC SEQ ID NO: 6 |

Examples of the second group, which recognize asymmetric sequences, include:

| ENZYME | RECOGNITION SEQUENCE AND CLEAVAGE SITE |
|---|---|
| EcoRII | CCAGG (0,5) |
| BstNI | CC ↓ AGG |
| AvaII | G ↓ GACC |
| NciI | CC#GGG |
| TfiI | G ↓ AATC |

Examples of the third group, which recognize sequences that are removed from the site of scission, include:

| ENZYME | GROUP III RECOGNITION SEQUENCE AND CLEAVAGE SITE |
|---|---|
| BbvI | GCAGC (8/12) |
| BbvII | GAAGAC (2/6) |
| BinI | GGATC (4/5) |
| BsmAI | GTCTC (1/5) |
| BsmI | GAATGC (1/−1) |
| BspMI | ACCTGC (4/8) |
| Eco31I | GGTCTC (1/5) |
| FokI | GGATG (9/13) |
| GdiII | YGGCCG (−5/−1) |
| GsuI | CTGGAG (16/14) |
| HgaI | GACGC (5/10) |
| HphI | GGTGA (8/7) |
| Ksp632I | CTCTTC (1/4) |
| MboII | GAAGA (8/7) |
| MmeI | TCCRAC (20/18) |
| MnlI | CCTC (7/7) |
| PleI | GAGTC (4/5) |
| SfaNI | GCATC (5/9) |
| TaqII | GACCGA (11/9) or CACCCA (11/9) |
| Tth111II | CAARCA (11/9) |

Examples of the fourth group, which cut bluntly, include:

| ENZYME | GROUP IV RECOGNITION SEQUENCE AND CLEAVAGE SITE |
|---|---|
| AhaIII | TTT ↓ AAA |
| AluI | AG ↓ CT |
| BalI | TGG ↓ CCA |
| CviJI | RG ↓ CY |
| Eco47III | AGC ↓ GCT |
| EcoRV | GAT ↓ ATC |
| FnuDII | CG ↓ CG |
| HaeI | WGG ↓ CCW |
| HaeIII | GG ↓ CC |
| HpaI | GTT ↓ AAC |
| MstI | TGC ↓ GCA |
| NaeI | GCC ↓ GGC |
| NlaIV | GGN ↓ NCC |
| NruI | TCG ↓ CGA |
| NspBII | CMG ↓ CKG |
| PmaCI | CAC ↓ GTG |
| PvuII | CAG ↓ CTG |
| RsaI | GT ↓ AC |
| ScaI | AGT ↓ ACT |
| SmaI | CCC ↓ GGG |
| SnaBI | GTA ↓ TAC |
| SspI | AAT ↓ ATT |
| StuI | AGG ↓ CCT |

Examples of the fifth group include the following examples:

| Cleavage Sequence | Enzyme Combinations | Recognition Sequences |
|---|---|---|
| N ↓ GATC N | BglII | A ↓ GATC T |
|  | Bcl I | T ↓ GATC A |
|  | BamH I | G ↓ GATC C |
| N ↓ CATG N | Nco I | C ↓ CATG A |
|  | BspH I | T ↓ CATG A |
| N ↓ CTAG N | Nhe I | G ↓ CTAG C |
|  | Avr II | C ↓ CTAG G |
|  | Xba I | T ↓ CTAG A |
|  | Spe I | A ↓ CTAG T |
| N ↓ CGCG N | Mlu I | G ↓ CGCG C |
|  | BssH II | A ↓ CGCG T |
| N ↓ CCGG N | Xma I | C ↓ CCGG G |
|  | Bsp MII | T ↓ CCGG A |
|  | Age I | A ↓ CCGG T |
| N ↓ TCGA N | Xho I | C ↓ TCGA G |
|  | Sal I | G ↓ TCGA C |
| N ↓ TGCA N | Pst I | C ↓ TGCA G |
|  | Nsi I | A ↓ TGCA T |

All of these enzymes (other than blunt and symmetric cutters) expose 1-5 potentially asymmetric positions on the freed sticky end after restriction. By utilizing growth enzymes whose recognition sites either are interrupted, asymmetric, blunt cutting, form symmetric pairs, or are distal to the cutting site, it is possible to destroy or eliminate the restriction site when a new molecule is ligated to the cohesive end. This is a desired property of "growth enzymes" and a critical property in forming more complex structures.

The term "growth enzyme" may also include a combination of enzymes, chemicals or enzymes and chemicals which perform any number of reactions to yield the same result. For example, a symmetrically cleaving endonuclease that does not have a mate for site destruction, as do those in Group V, is generally not considered a growth enzyme because any polynucleotide which hybridizes to the sticky end will inherently reform the restriction enzyme's recognition site. However, if one were to eliminate all or part of the single stranded portion, for example with a single strand nuclease, then the blunt end or shorter sticky end may be ligated to a molecule such that the recognition site is not reformed.

Another way in which even symmetrically cleaving endonucleases can be used is to chemically alter the recognition site, preferably after cleavage and prior to ligation, so that it is not recognizable by the enzyme. A simple way to do this is by adding a chemical moiety to a recognition site nucleotide. Methylation of DNA is a well known technique and may be used for this purpose. The restriction enzyme AluI recognizes and cleaves AGCT but not AG$^{m5}$CT. $^{m5}$C stands for 5-methylcytosine. One can methylate the site AGCT with the methylase M.AluI to form the non-cleavable AG$^{m5}$CT. EcoRI is another example which cleaves GAATTC but not GA$^{m6}$ATTC. $^{m6}$A stands for 6-methyladenine. Methylase M.EcoRI will form the non-cleavable GA$^{m6}$ATTC Numerous other examples of methylases and restriction enzymes which do not cleave methylated sites exist.

Other chemical modifications are also possible. Since the single stranded sticky end frequently contains part of the recognition site and is more accessible for chemical modification than the hydrogen bonded double strands, one may use a wide variety of techniques to derivatize the nucleotides so as to inactivate the recognition site. Thus, derivatization of the sticky end left after cleavage by a symmetrically cleaving restriction enzyme, prior to ligation, will leave a derivatized recognition site which is no longer recognized by the growth enzyme. The number of possible derivatives is very large. For the purposes of this application, the combination of steps yielding this result also constitute a "growth enzyme" even though plural steps and possibly plural enzymes are needed.

While these enzymes were designed for cleaving DNA, other enzymes may also be used for cleaving other polynucleotides. For example, RNA splicing enzymes and even non-enzyme chemicals which cleave the polynucleotide at a relatively specific site, may be considered "growth enzymes" for the purpose of the present invention.

Thus, for the purpose of the present specification and claims, the term "growth enzyme" is intended to comprehend any enzyme or combination of enzymes and/or chemicals in multiple steps, which will cleave a polynucleotide at a well-defined site to leave a cleaved end which, when ligated to another polynucleotide, will not retain a site recognizable by the same growth enzyme used to make the initial cleavage.

The new synthetic scheme of the present invention makes the newly formed edge immune to attack from traces of the restriction enzyme at a later time. Elimination of the restriction site allows repeated use of the same restriction enzyme which provides greater flexibility in further modification. When using a restriction enzyme which cuts bluntly, one may ligate double stranded structures which were never cleaved with such an enzyme.

Another advantage of this procedure is that the growing molecule is always a closed, topologically-bonded molecule, after successful ligation takes place. This allows the product to be subjected to vigorous treatment (e.g., heat denaturation or phenol extraction to remove enzymes), without irreversibly disrupting the structure. The unique closed-covalent nature of the successfully ligated product means that failures of addition will be susceptible to treatment with an exonuclease (e.g., exonuclease III) or other similar means, to destroy unsuccessfully ligated molecules, as shown in FIG. 3. Because the successful ligation results in a closed object, exonuclease III treatment only destroys the failure object, not the successful ligation, which can then continue. This treatment is logically analogous to 'capping' in solid-phase oligonucleotide synthesis (Caruthers, supra.). Removal of unsuccessfully ligated material (failure products) is a great aid in purification of the target product. Even if the exonuclease does not completely destroy the unligated products, the result is sufficiently different that one may easily separate the two products.

The general nature of the present invention will best be understood from a consideration of the drawings. Referring first to FIG. 1A, a polynucleotide chain of predetermined structure is synthesized such that it will fold over and hybridize to itself, thereby forming a hairpin loop. The predetermined sequence is selected such that the hairpin loop contains a recognition and cleavage site for an enzyme which recognizes an interrupted sequence.; In the particular example shown in FIG. 1A, the loop (SEQ ID NO:17) is constructed with a recognition and cleavage site for the enzyme BglI. After allowing the BglI enzyme to cleave the double stranded segment, and the hairpin end is removed, an asymmetric sticky end forms. A second polynucleotide chain of a second predetermined sequence is synthesized so as to form a double-stranded segment with an asymmetric end (sticky end) which is complementary to, and thus capable of hybridizing with, the sticky end of the first segment. The longer of the two strands of this construct has been designated SEQ ID NO:18. The sequence of the second segment is selected to have a proper choice of nucleotides near the sticky end such that the original BglI recognition site is not reformed upon ligation to the first segment. Thus, after hybridization and ligation, a single long double-stranded segment is obtained (the two strands of which have been designated SEQ ID NO:19 and SEQ ID NO:20) retaining no recognition and cleavage site for the enzyme BglI.

Figure 1B:
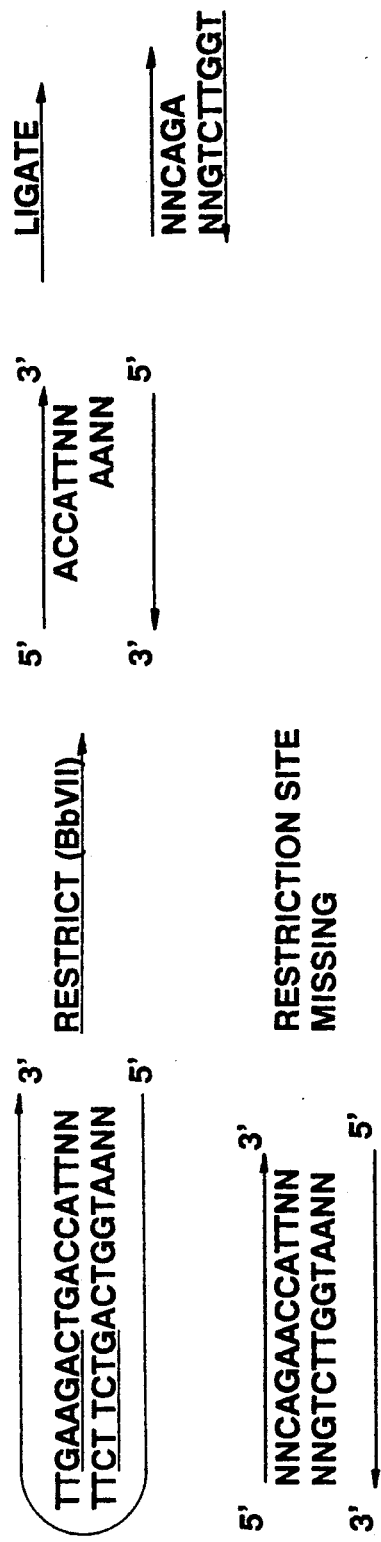

FIG. 1B is another example of growth enzyme cleavage using an enzyme which recognizes a sequence which may be removed from the site of cleavage. In this situation, the first nucleotide chain which is synthesized is constructed so as to leave the recognition site closer to the hairpin loop end of the segment than the cleavage site. Thus, once cleaved by the preselected enzyme, the removed hairpin loop containing the recognition site may be discarded. As the first segment is preferably attached to a solid support, it is an easy matter to simply wash away the cleaved portions. In the specific example of FIG. 1B, the loop (SEQ ID NO:21) is constructed with a recognition site for the enzyme BbvII. When a second previously synthesized double-stranded polynucleotide of predetermined structure (the longer of the two strands of which being designated as SEQ ID NO:22) with a sticky end complementary to the sticky end of the first segment left after BbvII cleavage, is added to the cleaved double-stranded first polynucleotide, the two become ligated when T4 or other ligase and cofactors such as ATP are added. The two strands of the formed segment have been designated as SEQ ID NO:22 and SEQ ID NO:23, respectively. By choosing almost any nucleotides except those with the recognition site for BbvII in the second segment, the recognition site no longer exists. The segments in both FIG. 1A and FIG. 1B may be much longer than depicted in the figures, provided that they have the growth enzyme recognizable ends as discussed above.

It should be understood that when synthesizing the various hairpin loops and other structures for use in the present invention, the choice of sequence is substantially arbitrary, provided that strands intended to be opposite one another are complementary, and provided that the predetermined restriction sites are at predetermined places in the structure. It is preferable to use previously described symmetry minimization algorithms (Seeman, N. C., *J. Biomol Str. & Dyns.*, 8;

573-581 (1990); Seeman, N. C., In: *Biomolecular Stereodynamics*, ed. R. H. Sarma, Academic Press, pp. 269-277 (1981); Seeman, N. C., *J. Theor. Biol.* 99: 237-247 (1982)) in order to optimize the sequences to avoid unwanted cross-hybridization.

The length of the strands is not critical, though for the initial phase, short strands are preferred. The choices of sticky ends and growth enzyme sites are also not critical, provided that they are compatible. All specific examples used throughout the specification are merely for the purpose of illustration and not limitation.

To facilitate easy separation and purification, the developing structure is synthesized on a solid phase. Simple washing separates the developing structure from all unwanted reagents. Any means of linking a polynucleotide to a solid phase may be used, but for more efficient production, the linkage should be easily cleavable under conditions which do not harm the structure. As is illustrated in FIG. 2A, one may chemically couple a crosslinked double strand to a solid phase to provide support and space from the solid phase. The linkage must withstand denaturing conditions without having its strands separate.

FIG. 2A illustrates the preparation of an initial branched DNA structure on a solid support having two hairpin loops, each loop having a different growth enzyme restriction site. The solid support is illustrated by the grey ball 10. A single strand of polynucleotide 11 is synthesized directly on the solid support and is designated in FIG. 2A as S-Strand-1. A cross-linked linker section 20 is prepared in a manner such that a sticky end 16 complementary to strand 11 extends therefrom at one end. Thus, stand 12 and strand 14, designated X-Strand-1 and X-Strand-2, respectively, are synthesized with complementary structures except for the respective sticky end extensions 16, 18 and these are cross-linked such as by psoralen cross-linking. The cross-linked linker section 20 is then ligated to strand 11 on the solid support 10 to form a non-denaturable double helical base 22 for the subsequent synthesis.

Any desired structure may be ligated to this base depending upon the nature of the structure to be ultimately constructed. The structure 24 added to the base 22 in FIG. 2A is called J-Strand-1, and has two hairpin loops 28 and 30. The open end of structure 24 is constructed so as to have a sticky end 26 complementary to the overhanging sticky end 18 of base 22 so as to hybridize thereto and permit the two segments to be ligated to one another to form structure 32.

Structure 24 is initially synthesized as a long single-stranded polynucleotide structure whose sequence is carefully chosen so as to cause it to hybridize upon itself and form the branched structure as shown. An example of a sequence for structure 24 is shown as J-Strand-1 in Example 1, Table 1, hereinafter. This structure is illustrated in two-dimensional form in FIG. 2B. Note that the restriction enzyme recognition site on hairpin loop 28 is that for AlwNI (CAGNNNCTG) SEQ ID NO:1 which is illustrated within a box. The restriction enzyme recognition site for hairpin loop 30 is that for the enzyme PflMI (CCANNNNNTGG) SEQ ID NO:5 which is also illustrated as being within a box. The underlined portions are the portions of the hairpin loop which are excised upon being subjected to the respective growth enzymes.

Figure 2B:
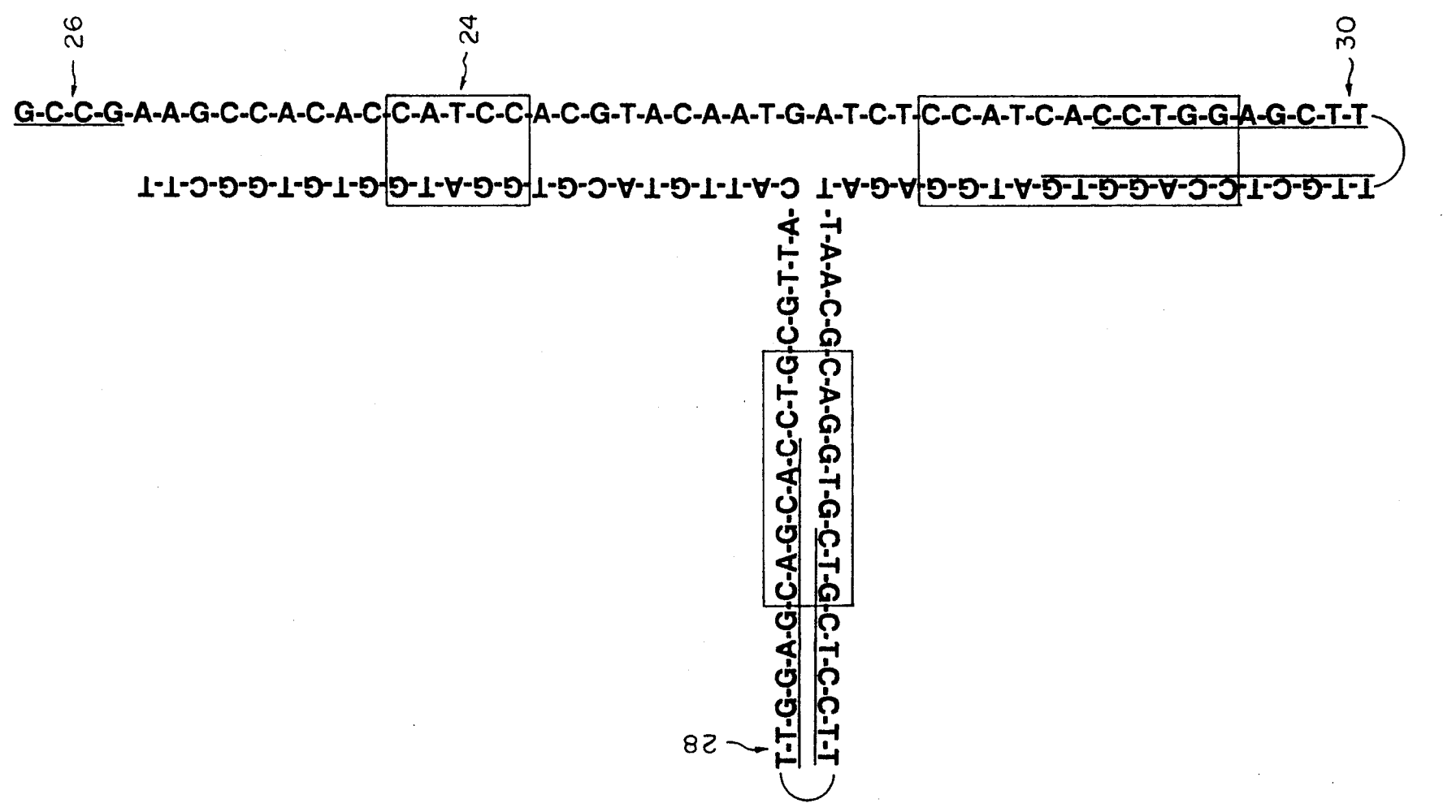

The next steps in the procedure are illustrated in FIG. 3. Hairpin loop 28 of structure 32 is cleaved with its respective growth enzyme A. In the example of FIG. 2B, this would be AlwNI. Because hairpin loop 30 does not have the recognition site for this particular growth enzyme, it will not be affected. Only hairpin loop 28 will be cleaved to form structure 33 with available sticky end 34. Another segment 36 may then be mixed with the solid phase 33. The segment 36, which is exemplified as J-Strand-2 in Example 1, has an available sticky end 38 complementary to sticky end 34, and may contain two additional hairpin loops 40 and 42, each having a restriction site recognizable by preselected growth enzymes C and D, respectively. Restriction enzymes C and D may be the same or different from enzyme A, depending on the desired final structure. When successfully ligated, the complex solid phase structure 44 is obtained.

In order to eliminate any structure which did not successfully ligate with segment 36, exonuclease III is added to digest the molecule 33 which is not covalently closed. Since the desired structure 44 is covalently closed, it is unaffected by this enzyme. However, the products which are not properly formed are digested by the exonuclease to yield structure 46, and are not available for the later steps in the process.

Figure 4:
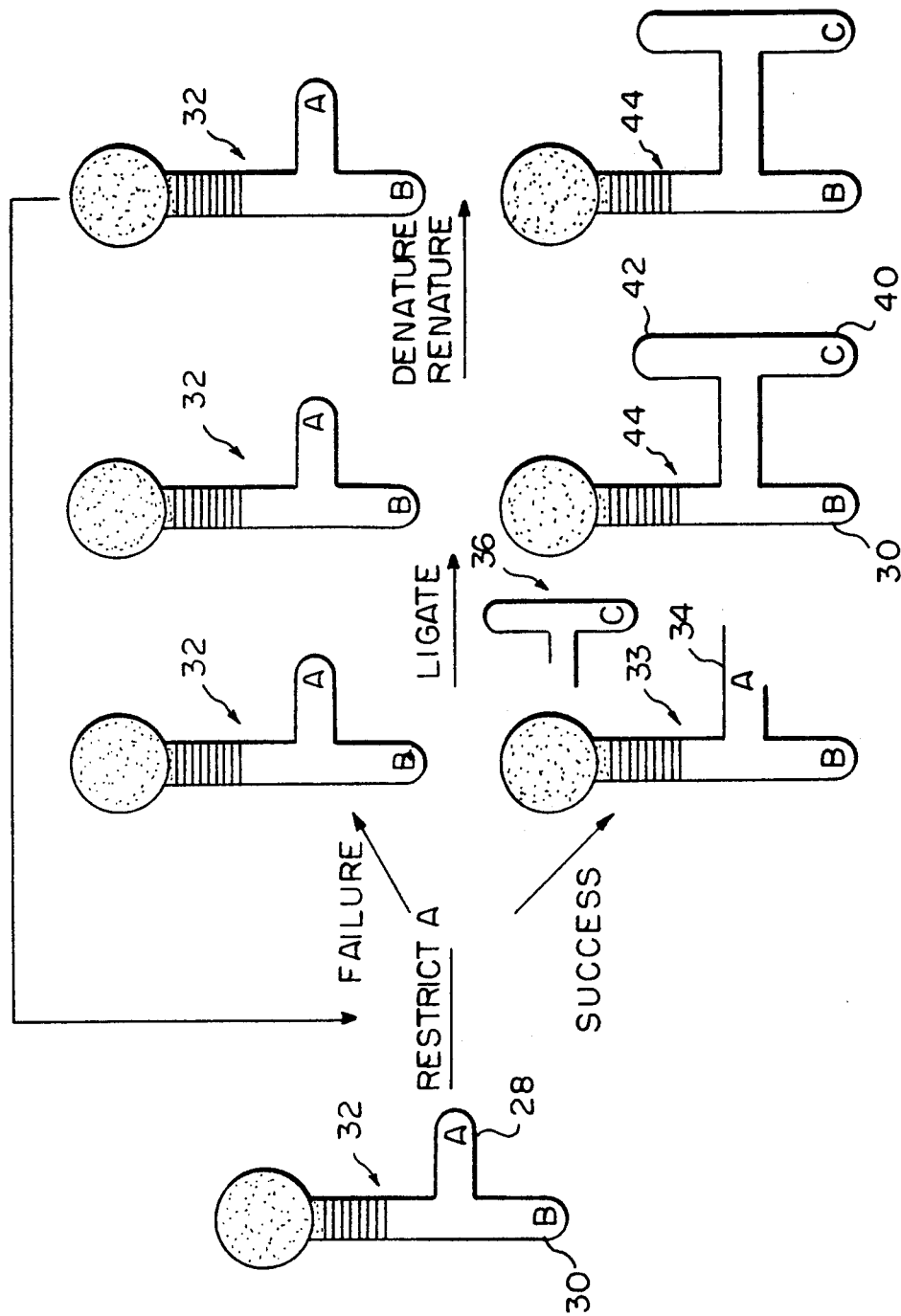
FIG. 4 is a diagram showing a protocol for a solid-state synthesis using a restriction rescue procedure. The strategy of this method is illustrated for the restriction and ligation.
Figure 5:
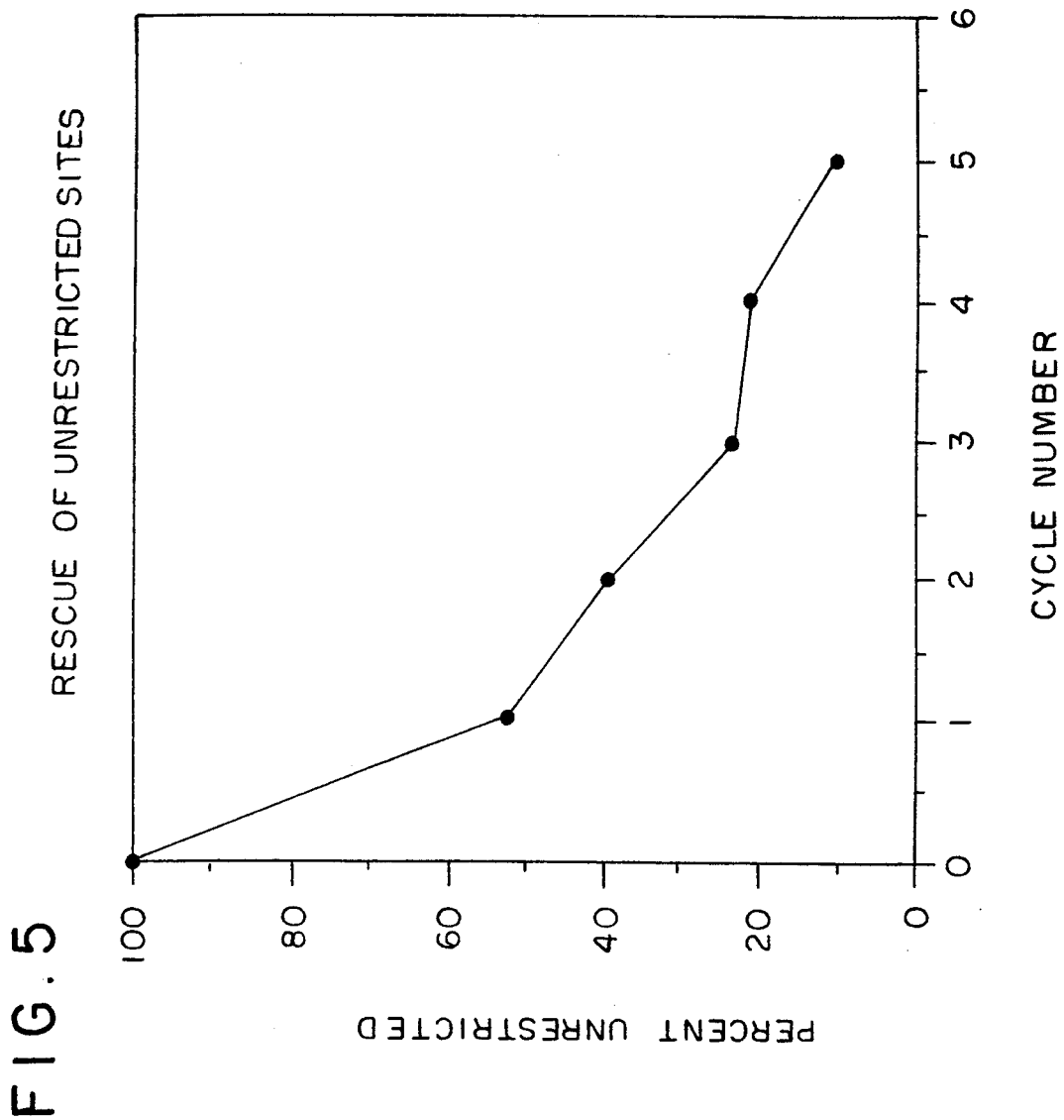
FIG. 5 is a graph illustrating the efficiency of repeating a restriction rescue procedure when using BglI digestion of the product of the first ligation. The graph shows the results from repeating the procedure for five cycles of restriction, ligation, denaturation and renaturation.

FIG. 4 shows a protocol using a restriction rescue procedure. This protocol is operable when the structure 36 being ligated to the sticky end 34 of solid structure 33, does not contain a recognition site which is the same of that which is on hairpin loop 28 of structure 32. Thus, hairpin loop 40 has a recognition site for enzyme C which is not the same as enzyme A used to restrict hairpin loop 28. In FIG. 4, successful restriction and ligation proceeds as in FIG. 3. Those molecules that fail to be restricted, however, may be recycled after subjecting them to denaturation-renaturation so as to expose and/or form their sites more perfectly. Restriction using restriction enzyme A may then be repeated followed by repetition of the ligation step in order to produce additional structure 44. This process may be repeated as many times as necessary to drive the reaction to greater completion. FIG. 5 shows the efficiency of repeating the restriction-rescue procedure. When the recycling and reuse of restriction enzyme A is completed, the exonuclease step shown in FIG. 3 may be used to eliminate the cleaved molecules with failed ligation.

The entire process is particularly useful when using small amounts of enzyme or when the enzyme is less efficient. The graph of FIG. 5 illustrates the use of 40 units of BgII with the product of the first ligation of J-Strand-3 to J-Strand-1. For this particular choice of reagents, improvement was noticed even after five cycles of restriction, ligation, denaturation and renaturation. Other enzymes such as AlwNI display greater efficiency in this system. The choice of which reactions need this recycle step would depend on the choice of enzymes, their concentrations, the molecule being acted upon, its fixed relation to the solid support and the reaction conditions.

FIG. 6 is a protocol showing the synthesis of a quadrilateral. The first steps are the same as shown in FIG. 3. Solid state structure 32, having hairpin loops 28 and 30, each having different restriction sites, is subjected to the restriction enzyme A for hairpin loop 28 to leave a solid state structure 33 with a sticky end 34. This is then ligated to structure 36 to form solid state structure 44. The hairpin loop 40 of structure 36 has a recognition site for growth enzyme C.

Structure 44 is then subjected to the restriction enzyme which recognizes the restriction site on hairpin loop 40, and the sticky end 43 is ligated to a complementary sticky end on a previously synthesized structure 48 to form structure 50. Hairpin loop 54 of structure 50, having a site for restriction enzyme E is then cleaved with the appropriate restriction enzyme, and additional structure 56 is ligated thereto to form structure 58.

Finally, two restriction enzymes are used to cleave hairpin loops 62 and 30. The structures of these loops have been preselected so that the sticky ends which are left after restriction are complementary to one another so that they may be ligated together to form the quadrilateral 64. In unusual circumstances, such as when one is modifying an existing structure, one may not have compatible hairpin loops adjacent to one another, such that sticky ends after cleavage of hairpin loops 30 and 62 are not complementary. In such a case, a short linker with sticky ends for both cleaved arms may be synthesized, added and ligated to close the quadrilateral.

In FIG. 6, it is seen that restriction enzyme A produces sticky end 34, restriction enzyme C produces sticky end 43, etc. The sticky end produced by each enzyme A, C and E may be the same so that the same sticky end 38 may be used on all of structures 36, 48 and 56, and any of structures 36, 48 or 56 could be used in the last step, as the sticky end obtained after cleavage with the appropriate growth enzyme will always be complementary to that obtained when loop 30 is cleaved by restriction enzyme B.

Using different enzyme restriction sites on arms 28, 40, 54 and 62 facilitates use of the restriction rescue procedure discussed above with respect to FIG. 4. For this purpose, only consecutive added structures must have different restriction sites. Every other structure may be the same site, and may indeed be identical structures. For example, in FIG. 6, restriction enzyme E may be identical to restriction enzyme A and restriction enzyme C may be the same as restriction enzyme G. Thus, structures 36 and 56 may be identical. If the restriction rescue operation is not used, enzymes A, C, E and G may be identical and all of structures 36, 48 and 56 may be the same. It is, of course, important that the growth enzymes A, C, E and G used to cleave loops 28, 40, 54 and 62 be different from the growth enzyme B which recognizes the site on hairpin loop 30.

The restriction sites on hairpin loops 42, 52 and 60, which are shown as being recognized by restriction enzymes D, F and H, respectively, may be selected to facilitate the addition of any desired additional structure, depending on the desired connectivity of the final product.

Plural molecular additions and the preparation of large molecules is exemplified in FIG. 7. Five structures, 100, 102, 104, 106 and 108 (FIGS. 7A-7E, respectively) are synthesized for use in this process. The solid state base structure 100, shown in FIG. 7A, has three arms, 112, 114 and 120. Arms 112 and 114 are open, and have complementary sticky ends designated 113 and 115 Arm 120 ends in a hairpin loop, having a recognition site cleavable by restriction enzyme Z. Structure 102, shown in FIG. 7B, has four arms, three of which are hairpin loops 118, 120, 122. The open arm 112 has the same sticky end 113 as in structure 100. Similarly, the downwardly extending loop 120 has a structure recognizable by restriction enzyme Z. The other two arms 118 and 122 are closed hairpin loops. Structure 104, shown in FIG. 7C, is similar to structure 102, except the leftwardly extending arm 116 is a closed loop and the arm 114 extending to the right has the same sticky end 115 as in structure 100. The downwardly extending arm 120 is the same as those in structures 100 and 102. The upwardly extending arm 122 may be the same or different as the corresponding upwardly extending arm in structure 102. Structure 106, shown in FIG. 7D, is similar to structure 100, except that the upwardly extending arm 126 is open and has a sticky end 125 which is complementary to the sticky end of arm 120 which is left after being cleaved by restriction enzyme Z. Structure 106 includes a downwardly extending arm 120 which is the same as the downwardly extending arms in structures 100, 102 and 104, and left and right extending arm 112 and 114 which are the same as those of corresponding structure 100. Finally, structure 108, shown in FIG. 7E, has a downwardly extending arm 124 with a sticky end 123 complementary to the sticky end 125 on arm 126 of structure 106. Left, right and upwardly extending arms 116, 118, and 122, respectively, are closed loops and may or may not have the same structure as the corresponding closed loops of structures 102 and 104.

In the first step of the procedure illustrated as FIG. 7F, solid state structure 100 is mixed with structures 102 and 104, and ligated so as to form the structure 130. It can be seen that structure 130 has three downwardly extending arms 120, each having a common growth enzyme site. Thus, when structure 130 is subjected to growth enzyme Z and then ligated with structure 106, three molecules of structure 106 are added simultaneously in order to form structure 132. If desired, one may repeat this three-fold addition, by cleavage with restriction enzyme Z and ligation with structure 106, indefinitely to make a long ribbon. Alternatively, the structure can be expanded in two dimensions so as to form a sheet by ligating structure 132 with additional molecules of structure 102 and 104 to expand to the left and right and form structure 134. Those molecules that do not get through the last step may be heat killed to ensure a healthy growing lattice, and structure 108 may be ligated to the structure in order to anneal excess lateral additions. It can be seen that when the growth procedure is repeated, this time five molecules of structure 106 will be added simultaneously to form structure 136 followed by repeated ligation with structure 102 and 104 for lateral expansion. This may be repeated as many times as necessary to make a large lattice structure.

As drawn, structures 102 and 104 expand the lattice by a single unit on each cycle. However, multimeric versions of 102 and/or 104 could also be used. For example, if hairpin loop 118 of structure 102 is cleaved to leave a sticky end 115 complementary to sticky end 113 of another structure 102 and these two structures are hybridized and ligated, one will have a dimeric structure having two upwardly extending arms 122, two downwardly extending arms 120, one arm 118 and one arm 112. Even longer versions could also be synthesized for use in this process. A multimeric version of structure 104 could be made in the same way and a multimeric version of structure 106 could be made in a similar manner by extending downwardly. Use of such multimeric structures in place of corresponding structures 102, 104 and 106 in the present process would expand the growing structure by multiple units either in width or length.

While the procedure of the present invention was primarily designed for making chemical structures of predetermined geometry having no relationship in any way to what the polynucleotide sequences might code for if in a biological system, the process of the present invention can also be used to synthesize long double-stranded DNA molecules for use in recombinant DNA procedures and genetic engineering techniques. Using the techniques of the present invention, it is only necessary to synthesize relatively short segments having hairpin loops and predetermined cleavage sites which may then be cleaved and ligated to extend the structure one-dimensionally so as to eventually synthesize a double-stranded DNA structure of indefinite length which may be extremely long with a predefined accurate sequence. This technique is also useful in adding radioactive or other labeling to a polynucleotide.

Referring to FIG. 8, one can start with the solid phase cross-linked support 22 from FIG. 2A. The sticky end 18 extending therefrom preferably has the first nucleotides of the gene sequence which it is desired to synthesize. A structure 140 is then synthesized, having a hairpin loop 144 and a sticky end 142 complementary to the sticky end 18 of structure 22. The sequence of structure 140 is preselected so as to have the double-stranded sequence of the gene of interest throughout region 146 up to the cleavage site 147. Preferably, the hairpin loop 144 contains an enzyme site such as that shown in FIG. 1B, in which the entire recognition site is removed by the enzyme. In this manner, all of the nucleotides which are left after cleavage are predetermined coding nucleotides for the gene of interest. Once structure 140 is ligated to structure 22 and hairpin loop 144 is cleaved at cleavage site 147, one is left with solid state structure 148 having a sticky end 150. The structure of the gene of interest can then be further extended by synthesizing another piece 154 having a sticky end 152 complementary to the sticky end 150 and having a hairpin loop 156 with another restriction site which may be the same or different as the restriction site of hairpin loop 144. The double-stranded structure can then be extended indefinitely with every nucleotide in the final product having a coding significance and without ever having to synthesize any polynucleotide strands longer than that necessary to obtain the intermediate segments 140, 154, etc. Once the gene of interest is finished, one may cleave it from the solid phase by any standard process.

It is also possible to construct a sequence 158 with a hairpin loop 162 at the end intended to ligate to structure 148. In this embodiment the sequence 158 is selected such that the loop 162 is cleavable by a preselected restriction enzyme to leave a sticky end complementary to sticky end 150 and to otherwise have the double-stranded structure for the segment of the gene of interest. The failure elimination and rescue procedures of FIGS. 3 and 4 can also be used when synthesizing genes in one dimension.

This technique has significant advantages over conventional solid phase gene synthesis as it is much more effective to synthesize shorter strands than longer strands. Unlike synthesizing portions of the gene separately and linking them up, one need only synthesize single strands. Because of the hairpin formation and the method of the invention, these appear to be double strands during ligation. The failure elimination procedure should result in greater product purity than conventional methods.

Throughout the examples, small few arm structures are used for simplicity of explanation but it is to be understood that vastly more complex configurations may be used. The only limitations as to the structure appears to be the physical properties of the polynucleotides themselves. Ma et al (supra) and Petrillo et al., *Biopolymers*, 27: 1337-1352 (1988) disclose that junctions can be stable at angles of as little as 60°. This permits up to 22 different arms from the same junction when considered in three dimensions. If more arms are desired, one may simply have multiple junctions. Thus, the molecule being added with any number of junctions may be quite complex.

The molecule being added may be so complex that the techniques of the present invention may need to be employed to form a molecule to be added to the growing structure. One may even link two or more finished structures together to form a type of polymer or polymers analogous to railroad cars linked together. This may be done by leaving two or more hairpin structures containing a growth enzyme site. These may be cleaved with a growth enzyme and when ligated together, the entire solution may be polymerized.

Another advantage to the current invention is that it is not limited by the ability to synthesize very long strands of DNA. By using enough cycles, one can add any number of molecules on the growing structure without the usual technical limitations of conventional DNA synthesis. The polynucleotide structures so formed may be very small, in the tens of nanometers, or easily prepared to be greater than one micron in size. With automation and patience, it is conceivable to prepare a macroscopic (millimeters in size) structure. Larger structures may prove to be too time consuming or costly but are theoretically obtainable for specialized purposes. The measurements for the purposes of this application may be considered to be the longest dimension of the structure formed.

The present invention is not limited to having only one molecule at a time being added to a developing structure. If the starting material at each step has multiple sites for one or more growth enzymes, one may simultaneously cleave these using one or more of these enzymes and thereby add plural molecules to the developing structure. As displayed in FIG. 7, an entire row of molecules may be simultaneously added to a developing structure. By using a combination of polynucleotide structures shown in the previous figures, the matrix is expanded in one or two dimensions. One may lengthen the developing structure in a different direction as well. While not shown in FIG. 7, the structure may be caused to grow in additional directions as well at any step by adding a molecule with a growth enzyme containing hairpin loops pointing above or below the plane of the paper. After enough expansion cycles, one could be adding thousands of additional molecules simultaneously. While this example shows adding very simple four armed polynucleotides, the molecules being added could be much larger and more complex. They may also constitute a heterogeneous mixture of molecules.

While this application refers to polynucleotides, it should be appreciated that this refers to both DNA and RNA and hybrids of the two. The structure need not resemble anything which can theoretically be made from nature.

A particular strand may employ bases other than the standard five, adenine, cytosine, guanine, thymine and uracil. Derivatized (e.g., methylated) and other unusual bases such as iso-guanine, iso-cytosine, amino-adenine, K, X, π, (Piccirilli et al, (1990) 343, 33-37), inosine and other derivatives of purine and pyrimidine may be used. A preferable feature in the selection of the bases is that they are capable of interacting with a base opposing them to form a specifically paired attraction. In natural DNA and RNA, hydrogen bonding forms this interaction. However, opposite ion charges, hydrophobic interactions and Van der Waals forces may also be acceptable forms of interaction. These interactions expand the choices over naturally occurring bases to give a wider assortment of physical properties.

Within a particular strand, the heterocyclic base may be entirely missing from the sugar moiety. This may be particularly desirable where the strands bend, form a junction or where one desires fewer forces holding the strands together.

While the molecules employed in this invention generally have a double stranded region recognized by a restriction endonuclease, the molecules may have virtually anything attached to them. Note that biotinylated DNA has previously been used to assist in attaching a label to DNA used as a hybridization probe. The molecule employed may be quite large and only have a small "tail" of double stranded polynucleotide containing a growth enzyme site. The method of the invention permits the easy addition of such a molecule to an existing structure with a suitable double stranded polynucleotide.

Linkers with plural ends ligatable to plural restriction sites may be employed to link diverse structures. Internal cyclizations are also likely to use a linker. While sticky ends on both the structure and the linker are desirable, they are not required. Typically, linkers have at least one portion being a double stranded polynucleotide, but other different chemical moieties are acceptable.

A particular strand need not have a single contiguous ribose-phosphate or deoxyribose-phosphate backbone. One may employ a simple inorganic or organic moiety or polymeric spacer between segments of polynucleotides. Spacers such as polyethylene, polyvinyl polymers, polypropylene, polyethylene glycol, polystyrene, polypeptides (enzymes, antibodies, etc.), polysaccharides (starches, cellulose, etc.), silicones, silanes and copolymers, etc., may be employed. An example of such a hybrid structure is dodecadiol having phosphoramidite at one end. This structure has been inserted covalently instead of 4 T nucleotides to form a hairpin loop in a fashion similar to the nucleotides it replaces. See Mitchel J. Doktycz, Ph.D. Thesis (1991), University of Illinois, Chicago. The term "polynucleotide" is intended to cover all of these structures.

In nature and the field of molecular biology, double stranded DNA generally occurs in the B form. However, for the purposes of this invention it may be desirable for DNA or other double stranded polynucleotides to exist in the A, C, D or Z form. Various bases, derivations and modifications may be used to stabilize the structure in the A, C, D or Z form as well.

For regions outside the growth enzyme recognition and cleavage sites, the polynucleotide may be triple or more stranded provided that the bases or their analogues interact to form an attraction. Also plural strands may interact with other plural strands to form a rope-like structure.

The term double stranded means at least one portion of the molecule has polynucleotide hydrogen bonds to what appears to be a second strand. For example, if the molecule contains only one strand which has a self hybridizing region, such as a loop or hairpin or other double stranded region, it is considered double stranded as long as it contains a region resembling a double stranded molecule.

All molecules synthesized by this procedure necessarily contain an unclosed exocyclic arm when released from the support. The exocyclic arm may be closed by annealing a hairpin to it. Reagents and enzymes may be recovered from washes, if they are not inactivated, and reused.

The technique of the present invention permits a much greater flexibility in modifying existing structures, whether they are by addition of a side chain or cyclization of the existing structure, than previous techniques. With an overall yield of about 60%, the efficiency exceeds that of previous solution formation of quadrilaterals which has an overall efficiency of about 15%.

The polynucleotide being added may have as few or as many additional loops as desired. This permits the formation of virtually any structure one desires. Polygons and polyhedron are the simplest to imagine, but irregular shapes and extensive scaffolding or internal supports may be built into or later added to the developing structure. Multiple additions to the structure may be made simultaneously. This may cause the structure to grow rapidly and eventually even become macroscopic. Branched nucleic acid molecules offer one of the most direct routes to employ mass additions.

Once the structure is sufficiently large, internal connectors are advantageous to provide additional structural support. The connectors may be connected to part of a junction or may be added as a three arm junction in the middle of an arm. The simplest example of a structure to exemplify this is a six sided box or cube where the edges of the box are polynucleotide double strands and the corners are the junctions. One may connect diagonal corners using an internal connector, or one may connect corners on exactly the opposite side from the middle of the structure or one may connect adjacent, non-adjacent or opposite edges of the structure. Plural internal connectors may also be used for additional support. The internal connectors may be connected to themselves or by using yet another internal connector which does not necessarily connect to any outside edge. With structures more complex than a simple box or cube, one may design very complex, specialized and specific structures.

The structures produced may be used as nuclei for crystal formation. For an analogous situation, see Seeman, in: *Biomolecular Stereodynamics*, ed. Sarma, Academic Press, NY p. 269-277 (1981); Seeman, *Journal of Theoretical Biology*, 99: p. 237-242 (1982); and Seeman, *Journal of Biomolecular Structure a Dynamics*, 3: p. 11-34 (1985). Since any polygon could be synthesized, almost any polyhedron could likewise be synthesized. This gives one almost any shape needed to start crystal formation. Polynucleic acids are particularly well-suited for use as a scaffolding medium, since they are thick two nanometer diameter), stiff (Hagerman P. J., *Ann. Rev. Biophys. & Biophys. Chem.*, 17: 265-286 (1988)) molecules unlikely to be perturbed markedly by tethering smaller non-interactive molecules to it.

Another application for this structure is in the formation of polycatenated polymers. Cyclic DNA and RNA inherently have this structure; therefore, their applicability to construct the same may be done, including using derivatized polynucleotides and even with appropriate spacers as desired.

The structure also makes a suitable material for immobilizing enzymes and other catalysts. By employing an open design for the structure, one or more enzymes may be bound to the structure and still permit free mobility of substrates and products to and from the enzyme. Instead of binding the enzyme directly to the structure, the structure may form a cage to entrap the enzyme(s). This technique has additional advantages of not modifying the enzyme.

A particular advantage of this structure is that it can immobilize more than one enzyme in close proximity. Many enzymes interact together by cycling co-factors and having the product of one be a substrate for another. Holding enzymes in close proximity is what makes a living cell so effective at performing an enormous number of metabolic activities in an efficient, regulated and coordinated fashion.

Conventional enzyme immobilization techniques depend on random attachment and thus the solid phase particles formed are not uniform in either activity or structure. By contrast, one can attach a predetermined number of enzymes to the polynucleotide strands being added to form a structure with a fixed number and orientation of enzymes.

The structure may be so formed to create a mesh or screen-like material. This material can be used as a filter of very precise porosity. For added strength, plural layers of mesh may be linked together or a layer may be bound to any other conventional substrate.

The structures of and produced by the present invention have numerous three dimensional structural uses. Because of the minute size of the structures, they have application in the developing field of nanotechnology. A polyhedron alone or with internal supporting structures may act as a very small ball bearing and be used as a lubricant. Larger structures may be abrasives. Since the shape may conform to almost anything desired, a miniaturized version of nearly any machine or device may be made. Common structures include rough spheres, cubes, rods, wires, ribbons, tubes, thin sheets, combinations of any of these, etc. The techniques of the invention give such flexibility that one may attach a structure to any other structure during or after its creation to give complex articles.

More current uses include use as a solubilizer and stabilizer for chemicals, particularly pharmaceuticals. For example, a drug may be bound to the interior of a three dimensional polynucleotide structure. Since DNA degrades in acidic conditions and RNA degrades in alkaline conditions, one can direct the drug to be released in whatever part of the digestive system desired.

Furthermore, the interior of the structure may be made hydrophobic while the exterior is hydrophilic. This may permit hydrophobic chemicals or drugs to be solubilized in aqueous solutions. An analogous technique has been applied previously with steroids and hydroxy propyl β-cyclodextrin with success. The reverse situation may also be performed in organic solutions, such as by removing the bulk of the charges on the nucleic acids, e.g., by substituting the bulk of methyl phosphonates for phosphates.

Another expected use is to design a specific binding structure. Since the distances and charges may be controlled at will, one can construct a receptor for a chemical. This may act as an adsorbent for separation or purification. Alternatively, the structure may be labeled and used as a specific binding reagent as is conventionally used in the field of analytical chemistry. If the structure is designed to bind an unstable intermediate, it may act as a catalyst as has been done with monoclonal antibodies.

Other uses are mentioned in applicant's copending patent application U.S. Ser. No. 07/639,684, filed Jan. 10, 1991.

By adapting the synthesis to a solid-support, the complete removal of restricted hairpins by restriction enzymes, exonuclease III, or excess added DNA is achieved. Solid support-bound growing molecules are readily separated from reagents and cleavage products, particularly at stages when denaturing conditions are not practical. Purification in a solid-support context entails simple washing, rather than gel purifications that are inefficient and tedious. In addition, growing objects are isolated from each other, preventing cross-reactions between them; this feature permits the use of symmetric (Group V) and blunt (Group IV) restriction sites in cyclization reactions.

There are several advantages to the solid-support synthetic strategy outlined: (1) One can synthesize a complex object one edge at a time, thereby maximizing control over the products. Inherently intramolecular reactions such as cyclization, can be run separately from intermolecular additions. (2) The successfully ligated material in any step can be readily separated from that step's starting materials and reagents (including restriction enzymes) without a denaturing-gel purification. (3) Unsuccessfully ligated materials can be destroyed while the material is on the support. (4) Precious starting materials can be recovered and recycled if washes are saved. (5) The procedure is potentially easily automated, so that scale-up can be done. (6) There is no apparent limit on the type of starting material that can be used. It seems that individual junctions, or individual cyclic strands, or polygons, or 3-D, N-connected objects could all be added to the growing construct. (7) One can distinguish between intermolecular additions and intramolecular cyclizations and each can be controlled by using different concentrations and different growth enzymes. Thus, this methodology is useful in forming individual objects, 1-D chains, 2-D lattice nuclei, or 3-D lattice nuclei.

EXAMPLE 1: Materials and Methods

The following general procedures are used in the present examples. The sequences of the DNA molecules used have been assigned by the program SEQUIN (Seeman, N. C., *J. Biomol. Str. & Dyns.*, 8; 573–581 (1990)), which assigns sequences to branched molecules, according to previously described symmetry-minimization algorithms (Seeman, N. C., In: *Biomolecular Stereodynamics*. ed. by R. H. Sarma, Adenine Press, pp. 269–277 (1981); Seeman, N. C., *J. Theor. Biol.*, 99: 237–247 (1982)). DNA molecules are synthesized and deprotected by routine phosphoramidite procedures (Caruthers, M. H., In: *Chemical and Enzymatic Synthesis of Gene Fragments*, eds. Gassen, H. G. and Lang, A., (Verlag Chemie, Weinheim), pp. 71–79 (1982)), on an Applied Biosystems 380B automated DNA synthesizing machine. Conventional phosphoramidites are purchased from Applied Biosystems (Foster City, Calif.). Chemical 5' phosphorylation (indicated by PO$_4$ in the sequence) is done by the method of Horn and Urdea (Horn, et al., *Tet. Lett.*, 27: 4705–4708 (1986)).

The sequences of of the strands synthesized for use in these examples are given in Table 1. These sequences are merely representative of the very large number of possibilities.

subjected to rigorous treatment are denatured by heating to 90° C. and then renatured by slow cooling.

Ligations are performed in a solution containing 66 mM Tris-HCl, pH 7.6, 1 mM spermidine, 100 mM

TABLE 1

DNA SEQUENCES

| STRAND NAME | SEQUENCE | |
|---|---|---|
| S-Strand-1 | PO$_2$—*C—C—T—A—A—C—G—C—G*—T$_6$—T$_{16}$—SS | SEQ ID NO: 7 |
| X-Strand-1 | *A—A—A—A—A—A*—C—G—C—G—T—T—A—G—G—T—G—A—C—A—T—A—T—A—T—C—T—A—T—A—G—A—T—A—T—A—T—T—C—G—G—A—C—C | SEQ ID NO: 8 |
| X-Strand-2 | PO$_4$—C—G—G—C—C—G—G—C—G—G—T—C—C—G—A—A—A—T—A—T—A—T—C—T—A—T—A—G—A—T—A—T—A—T—G—T—C—A | |
| J-Strand-1 | G—C—C—G—A—A—G—C—C—A—C—A—C—C—A—T—C—C—A—C—G—T—A—C—A—A—T—G—A—T—C—T—C—C—A—T—C—A—C<u>—C—T—G—G—A—G—C—T—T—</u><br>T<u>—T—G—C—T—C—C—A—G—G—T—G—</u>A—T—G—G—A—G—A—T—T—A—A—C—G—C—A—G—G—T—G—C<u>—T—G—C—T—C—C—T—T—T—T—G—G—A—G—C—</u><br>A<u>—G—C—A—C</u>—C—T—G—C—G—T—T—A—C—A—T—T—G—T—A—C—G—T—G—G—A—T—G—T—G—T—G—G—C—T—T— | SEQ ID NO: 9<br><br><br><br><br><br>SEQ ID NO: 10 |
| J-Strand-2 | A—G—A—T—G—A—G—T—A—T—T—A—A—C—G—C—A—G—G—T—G—<u>C—T—G—</u><br><u>C—T—C—C—T—T—T—T—G—G—A—G—C—A—G—C—A—C</u>—C—T—G—C—G—T—<br>T—A—G—A—C—C—T—A—C—G—A—C—T—T—T—T—G—T—C—G—T—A—G—G—<br>T—C—A—T—A—C—T—C—A—T—C—T—<u>C—A—C</u>— | SEQ ID NO: 11 |
| J-Strand-3 | A—G—A—T—G—A—G—T—A—T—T—A—A—C—G—C—C—G—G—T—G—<u>C—G—G—</u><br><u>C—T—C—C—T—T—T—T—G—G—A—G—C—C—G—C—A—C</u>—C—G—G—C—G—T—<br>T—A—G—A—C—C—T—A—C—G—A—C—T—T—T—T—G—T—C—G—T—A—G—G—<br>T—C—A—T—A—C—T—C—A—T—C—T—<u>C—A—C</u>— | SEQ ID NO: 12 |
| L-Strand-1 | G—C—C—G—T—T—G—A—C—G—A—C—T—G—T—C—T—C—G— | SEQ ID NO: 13 |
| L-Strand-2 | C—G—G—C—C—G—A—G—A—C—A—G—T—C—G—T—G—A—A— | SEQ ID NO: 14 |
| A-Strand-1 | C—G—G—C—G—A—C—G—C—G—G—T—T—T—T—T—T—A—C—C—G—C—G—T—C | SEQ ID NO: 15 |

Sequences are presented 5'→3'. "PO$_4$" at the 5' end indicates chemical phosphorylation. "SS" indicates the Teflon-based solid support. Excisable hairpins embedded in longer strands are underlined. Exposed or exposable sticky ends are in bold italics.

S-Strand-1 is synthesized on a Teflon-based solid support (Lohrmann, et al., *DNA*, 3: 122-122 (1984)) (obtained from Glen Research, Sterling, Va.). The partially complementary molecules used in a psoralen-crosslinked linker between the solid support and the growing DNA object are X-Strand-1 and X-Strand-2.

To prepare the psoralen crosslinked linker, the protocol of Sinden and Cole (Sinden, et al., *DNA Repair, A Laboratory Manual of Research Procedures.* ed. by E. Friendlier and P. Hanawalt, Marcel Decker, Inc., 1A: pp. 69-87 (1981)) is modified as follows: 10 μg of X-Strand-1 and 7 μg of X-Strand-2 are mixed in 100 μL of a solution containing 40 mM Tris Acetate, pH 8.1, 20 mM Na acetate, 2 mM EDTA, 12.5 Mg acetate (TA-EMg) and 1 mM 4, 5', 8-trimethylpsoralen (Sigma) at 4° C. for 30 min. The solution is exposed to 360 nm irradiation produced by a UVGL-25 Mineralite lamp (Ultra-Violet Products, San Gabriel, Calif.) for 3-5 hours. The crosslinked material is separated from the un-crosslinked material by denaturing polyacrylamide gel electrophoresis.

Restrictions and ligations are done on the solid-support. At the end of the reaction, unwanted enzymes, unreacted ligation materials or freed digestion products are separated from the solid support by washing. Five cycles of washing are sufficient for the purposes of the next stage. Molecules on the support that have been MgCl$_2$, 15 mM dithiothreitol (DDT), 0.2 mg/mL nuclease free bovine serum albumin (BRL), to which 66 μM ATP has been added. 20-40 units of T4 polynucleotide ligase (U.S. Biochemical) are added, and the ligation proceeds at 16°-22° C. for 16-18 hours. The reaction is stopped by washing the solid support five times at 65° C. A 10-20-fold excess of added DNA is added for each available growing object on the support. Alternatively, ligations may be done by chemical catalysis as described in Ashley et al, *Biochemistry,* 30: 2927-2933 (1991).

For the restriction endonuclease digestions, restriction enzymes are purchased from New England Biolabs, and used in buffers suggested by the supplier, but usually in much larger quantities and for much longer times than recommended for unbranched DNA molecules. The reaction is stopped by washing the solid support five times at 50° C.; the lower temperature is used because the product is no longer covalently closed.

Exonuclease III digestion uses exonuclease III (U.S. Biochemical) in a buffer containing 50 mM Tris-HCl, pH 8.0, 10 mM 2-mercaptoethanol and 5 mM MgCl$_2$ at 37° C. The reaction is stopped by washing the solid support five times at 65° C.

All strands greater than 30 nucleotides in length are purified by polyacrylamide gel electrophoresis. Shorter strands are purified by preparative HPLC on a DuPont Zorbax Bio Series oligonucleotide column at room temperature, using a gradient of NaCl in a solvent system containing 20% acetonitrile and 80% 0.02M sodium phosphate. Fractions from the major peak are collected, desalted and evaporated to dryness. Molecules are prepared for use under native conditions by heating to 90° C., followed by slow cooling to equilibrate them to optimally hybridized structures.

EXAMPLE 2

Using the techniques above the support is prepared following the procedure in FIG. 2A. The first stage is the synthesis of S-Strand-1 11 directly o the Teflon-based support 10. X-Strand-1 12, partially complementary to strand 11 and partially to X-strand-2 14, is psoralen-crosslinked to X-Strand-2 14, which is then ligated to S-Strand-1 11, to form a non-denaturable double-helical base for the synthesis. This duplex is then ligated to J-Strand-1 24 to complete preparation of the support.

EXAMPLE 3

A quadrilateral is synthesized using the protocol shown in FIG. 6. Beginning with the support 32 containing J-Strand-1, alternate cycles of restriction and ligation are performed, always at the position indicated as having a site for restriction enzyme A, C, E or G in FIG. 6. Following the procedures in FIG. 4, one can repeat the process four times to produce a quadrilateral. The fourth step employs an extra growth enzyme B to cause cyclization of the molecule. The last molecule being added may have the same or a different site for circularizing the structure. The final step (not shown) is to cleave the structure from the solid phase by any means known.

Selection of the target product (triangle, quadrilateral, pentalateral,...) is determined by the point at which one chooses to restrict with growth enzyme B, exposing a sticky end complementary to that exposed by restriction with enzymes A, C, E and G. Previous work with 3-arm junctions indicates that a large number of different cyclic products can be produced from such components (Ma, et al., *Nucl. Acids Res.*, 14: 9745-9753 (1986)).

EXAMPLE 4

The 3-arm junction called J-strand-1 24, attached to the crosslinked duplex, contains AlwN I (CAGNNNCTG) SEQ ID NO:1 and PflM I (CCANNNNNTGG) SEQ ID NO:5 restriction sites for excision of hairpins and a Fok I (GGATG 9/13) site for removal from the support (as shown in FIG. 2B). The two 3-arm junctions with a single restriction site are J-Strand-2 36, containing an, AlwN I site and J-Strand-3 48, containing a Bgl I (GCCNNNNNGGC) (SEQ ID NO:2) site, which exposes the same GTG sticky end as the AlwN I site of J-Strand-2. In order to anneal the final closed quadrilateral, it may be necessary to put a double-stranded linker, composed of for example, L-Strand-1 and L-Strand-2, containing a BsmA I (GTCTC 1/5) site between the psoralen-crosslinked linker and J- Strand-1. In general, the restriction site that releases the molecule from the support is preferably on the link to the solid support instead of on the molecule, where traces of restriction endonuclease can prevent annealing. The strand that anneals the quadrilateral is A-Strand- 1.

EXAMPLE 5

Solid-phase synthesis of a square lattice is prepared by repeated use of the techniques of the present invention. Solid support and crosslink are prepared as before. The starting materials are illustrated in FIGS. 7A-7E and are synthesized as follows: the solid-state support with a junction attached 100; a right-expanding junction 102; a left-expanding junction 104; and layer-expansion junction 106. The first step is left and right expansion of 100 by 102 and 104 to obtain the tri-branched structure 130. Structure 130 is then restricted by restriction enzyme Z (Z), mixed with structure 106, and then ligated (L) to give structure 132 with the two squares. Adding additional 102 and 104 widens the array. Heat killing those that do not get through the last step ensures healthy growing lattices, and then restriction with enzyme Z, adding structure 106, and ligating (L) extends the two squares into a second row of four squares (structure 136). These are expanded in the next step with structure 102 and 104, and then the cycle repeats.

Alternatively, one could prepare a long ribbon of any width and length using this technique. Once the desired width is achieved, one simply caps the loose sites 113 and 115 and continues adding rows on the Z site loops. This may be repeated many times. Once completed, one may also form a tube by cyclization after cleaving both sides of the ribbon with a growth enzyme(s) recognizing sites on arms 116 and 118. If they are sticky they may self bind or a linker may be added to bind both sticky ends followed by ligation. The result is a tube shaped structure.

EXAMPLE 6

As shown in FIG. 8, a single stranded DNA 140 is synthesized so that it forms hairpin 144 having the following structure upon self hybridization: sticky end 142—recognition and cleavage site 143 for a restriction enzyme to eventually remove the gene from the solid support—a portion 144 of the gene of interest—cleavage site 145 for a growth enzyme—recognition site 146 for a growth enzyme—hairpin loop 147. Sticky end 142 of strand 140 is complementary to sticky end 18 on support 22. Strand 140 is added to the non-denaturable double helix solid support prepared in Example 2 and ligated thereto, using the techniques of Example 1 to form structure 148.

Another single stranded DNA 154 is synthesized so that it forms hairpin 156 having the following structure upon self hybridization: sticky end 152 which is complementary to the sticky end of structure 148 after it is cleaved with an appropriate growth enzyme—a second portion 153 of a gene of interest—a cleavage site 155 for a growth enzyme—recognition site 157 for the growth enzyme—hairpin loop 156. Structure 148 is cleaved with the growth enzyme recognizing its closed end following the conditions of Example 1. The solid phase is separated and washed from the solution. Structure 154 is added to the cleaved solid phase chain and their respective sticky ends are allowed to bind to each other. Ligase is added and the two molecules are ligated using the conditions in Example 1 to form new structure 170. Additional segments of the gene or genes of interest may be added by synthesis of additional strands, not shown, similar to strand 154 but having the next segment of the gene or genes of interest in place of segment 153 and adding them to the growing structure in the desired order until the complete gene or genes is formed. The formed double-stranded DNA may then be removed from the solid support via cleavage site 143.

As opposed to using strand 154, another single stranded DNA 158 may be synthesized having the structure: hairpin loop 160—recognition site 162 for a growth enzyme—cleavage site 164 for the growth enzyme—a portion 166 of the gene of interest—sticky end 168. Sticky end 168 is not complementary to the sticky end which results upon cleavage of hairpin 147 from structure 148. However, the sticky end which results after cleavage of hairpin 160 from strand 158 is complementary to the sticky end of structure 148. When a strand 158 is used, the hairpin 160 may be removed before removing strand 158 from the solid support on which it was synthesized. The resulting structure after ligation of strand 158 to structure 148 may be ligated directly to the next strand without first cleaving a hairpin loop as must be done with loop 156 when strand 154 is used.

In conventional gene synthesis, addition errors can occur and an entire segment may even end up missing. See Beattie, et al. *Nature*, 252:548-9 (1991). Conventional gene synthesis lacks any means for eliminating failure additions. In accordance with the present invention Exonuclease III may be added to structures of type 170, in the same manner as is shown in FIG. 3 to eliminate errors and increase accuracy in the gene sequence.

The foregoing description of the specific embodiments reveals the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. All references mentioned in this application are incorporated by reference.

---

What is claimed is:

1. A method for producing a polynucleotide structure, comprising:
   a) synthesizing a double-stranded polynucleotide with a hairpin loop at one end and containing a recognition site for a growth enzyme;
   b) cleaving said polynucleotide with the growth enzyme which recognizes the recognition site thereon;
   c) synthesizing another double-stranded polynucleotide with a hairpin loop at one end and containing, at the end opposite the hairpin loop, a sequence ligatable to said cleaved polynucleotide of step b), and, near the hairpin loop, a recognition site for a growth enzyme; and
   d) ligating said polynucleotide synthesized in step c) to said polynucleotide obtained in step b) to obtain an elongated double-stranded polynucleotide with a hairpin loop at one end and containing a recognition site for a growth enzyme.

2. A method in accordance with claim 1, further including the steps of, after said step d), repeating said steps b) to d) at least once, using the elongated polynucleotide in step d) as the polynucleotide which is cleaved in step b).

3. A method in accordance with claim 1, wherein said double-stranded polynucleotide synthesized in step a) is connected at the end thereof opposite the hairpin loop to a solid support.

4. A method in accordance with claim 1, wherein said synthesizing steps a) and c) comprise synthesizing a single stranded polynucleotide with a sequence selected so as to have complementary segments which will hybridize to one another to form said double-stranded polynucleotides with hairpin loops and having the desired growth enzyme recognition sites.

5. A method in accordance with claim 1, wherein said growth enzyme used in step b) is one which cleaves said polynucleotide leaving a sticky end on said polynucleotide after removal of the cleaved hairpin loop, and said polynucleotide synthesized in step c) has a sticky end, opposite said hairpin loop, which is complementary to the sticky end on the polynucleotide obtained in step b).

6. A method in accordance with claim 1, wherein said polynucleotide synthesized in step a) and/or said polynucleotide synthesized in step c) is a branched polynucleotide having at least three ends and at least two hairpin loops, each of said hairpin loops having near the loop thereof a recognition site for a growth enzyme.

7. A method in accordance with claim 1, wherein said recognition site on the polynucleotide synthesized in step a) and the recognition site on the polynucleotide synthesized in step c) are different and selected such that they are recognized by different growth enzymes.

8. A method in accordance with claim 1, wherein said recognition site on the polynucleotide synthesized in step a) and the recognition site on the polynucleotide recognized in step c) are recognizable by the same growth enzyme.

9. A method in accordance with claim 6, wherein said polynucleotide synthesized in step a) is a said branched polynucleotide and wherein said step b) comprises cleaving at least two of said recognition sites with appropriate growth enzymes, said step c) comprises synthesizing a number of said another polynucleotides corresponding to the number of hairpin loops cleaved in said step b), each of said another polynucleotides being ligatable to a respective one of said cleaved polynucleotide strands of said polynucleotide produced in step b), and said step d) comprises ligating said polynucleotides produced in step c) to the respective branches of the polynucleotide produced in step b).

10. A method in accordance with claim 9, wherein, in said step b), all of said hairpin loops of the polynucleotide produced in step a) are cleaved substantially simultaneously and, in said step d), all of said another polynucleotides are ligated to said polynucleotide produced in step b) substantially simultaneously.

11. A method in accordance with claim 1, wherein at least one of the recognition sites on the polynucleotide formed in step a) and in the polynucleotide formed in step c) is a recognition site for a growth enzyme which recognizes an interrupted sequence, a growth enzyme which recognizes an asymmetric sequence or a growth enzyme which cleaves the polynucleotide on the side of the recognition site which is opposite the site thereof nearest the hairpin loop.

12. A method in accordance with claim 1, wherein the sequence of the polynucleotide synthesized in step c) which is ligatable to said cleaved polynucleotide of step b) is selected such that the original recognition site of the polynucleotide before being cleaved in step b) is not reformed.

13. A method in accordance with claim 1 wherein the polynucleotide synthesized in step a) is synthesized on a solid phase support and remains on said support throughout steps b) and d).

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

CAGNNNCTG        9

( 2 ) INFORMATION FOR SEQ ID NO:2:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

GCCNNNNNGG C        11

( 2 ) INFORMATION FOR SEQ ID NO:3:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

CCANNNNNT GG        12

( 2 ) INFORMATION FOR SEQ ID NO:4:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear (i i) MOLECULE TYPE: DNA (x i) SEQUENCE DESCRIPTION: SEQ ID NO:4:

CACNNNGTG 9

(2) INFORMATION FOR SEQ ID NO:5:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:5:

CANNNNNTGG 10

(2) INFORMATION FOR SEQ ID NO:6:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:6:

GGCCNNNNNG GCC 13

(2) INFORMATION FOR SEQ ID NO:7:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:7:

CCTAACGCG 9

(2) INFORMATION FOR SEQ ID NO:8:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:8:

AAAAAACGCG TTAGGTGACA TATATCTATA GATATATTTC GGACC 45

(2) INFORMATION FOR SEQ ID NO:9:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:9:

CGGCCGGCGG TCCGAAATAT ATCTATAGAT ATATGTCA 38

( 2 ) INFORMATION FOR SEQ ID NO:10:

( i ) SEQUENCE CHARACTERISTICS:
        ( A ) LENGTH: 132 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

```
GCCGAAGCCA CACCATCCAC GTACAATGAT CTCCATCACC TGGAGCTTTT GCTCCAGGTG      60
ATGGAGATTA ACGCAGGTGC TGCTCCTTTT GGAGCAGCAC CTGCGTTACA TTGTACGTGG     120
ATGGTGTGGC TT                                                         132
```

( 2 ) INFORMATION FOR SEQ ID NO:11:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

```
AGATGAGTAT TAACGCAGGT GCTGCTCCTT TTGGAGCAGC ACCTGCGTTA GACCTACGAC      60
TTTTGTCGTA GGTCATACTC ATCTCAC                                          87
```

( 2 ) INFORMATION FOR SEQ ID NO:12:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

```
AGATGAGTAT TAACGCCGGT GCGGCTCCTT TTGGAGCCGC ACCGGCGTTA GACCTACGAC      60
TTTTGTCGTA GGTCATACTC ATCTCAC                                          87
```

( 2 ) INFORMATION FOR SEQ ID NO:13:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

```
GCCGTTGACG ACTGTCTCG                                                   19
```

( 2 ) INFORMATION FOR SEQ ID NO:14:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

```
CGGCCGAGAC AGTCGTCAA                                                   19
```

( 2 ) INFORMATION FOR SEQ ID NO:15:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

CGGCGACGCG GTTTTTTACC GCGTC　　　　　　　　　　　　　　　　　　　　　　　25

( 2 ) INFORMATION FOR SEQ ID NO:16:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

NNGCCATGTA GGCTTTTGCC TACATGGCNN　　　　　　　　　　　　　　　　　　　30

( 2 ) INFORMATION FOR SEQ ID NO:17:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

NNAATGGTAC A　　　　　　　　　　　　　　　　　　　　　　　　　　　　11

( 2 ) INFORMATION FOR SEQ ID NO:18:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

NNGCCATGTA CCATTNN　　　　　　　　　　　　　　　　　　　　　　　　17

( 2 ) INFORMATION FOR SEQ ID NO:19:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

NNAATGGTAC ATGGCNN　　　　　　　　　　　　　　　　　　　　　　　　17

( 2 ) INFORMATION FOR SEQ ID NO:20:

( i ) SEQUENCE CHARACTERISTICS:
        ( A ) LENGTH: 36 base pairs
        ( B ) TYPE: nucleic acid
        ( C ) STRANDEDNESS: single (D) TOPOLOGY: linear (i i) MOLECULE TYPE: DNA (x i) SEQUENCE DESCRIPTION: SEQ ID NO:20:

TTGAAGACTG ACCATTNNNN AATGGTCAGT CTTCTT                                36

(2) INFORMATION FOR SEQ ID NO:21:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (i i) MOLECULE TYPE: DNA (x i) SEQUENCE DESCRIPTION: SEQ ID NO:21:

TGGTTCTGNN                                                             10

(2) INFORMATION FOR SEQ ID NO:22:

(i) SEQUENCE CHARACTERISTICS:
      (A) LENGTH: 14 base pairs
      (B) TYPE: nucleic acid
      (C) STRANDEDNESS: single
      (D) TOPOLOGY: linear (i i) MOLECULE TYPE: DNA (x i) SEQUENCE DESCRIPTION: SEQ ID NO:22:

NNCAGAACCA TTNN                                                        14

(2) INFORMATION FOR SEQ ID NO:23:

(i) SEQUENCE CHARACTERISTICS:
      (A) LENGTH: 14 base pairs
      (B) TYPE: nucleic acid
      (C) STRANDEDNESS: single
      (D) TOPOLOGY: linear (i i) MOLECULE TYPE: DNA (x i) SEQUENCE DESCRIPTION: SEQ ID NO:23:

NNAATGGTTC TGNN                                                        14